US 10,364,298 B2

(12) United States Patent
Reid et al.

(10) Patent No.: US 10,364,298 B2
(45) Date of Patent: Jul. 30, 2019

(54) *CLOSTRIDIUM DIFFICILE* LIPOTEICHOIC ACID AND USES THEREOF

(71) Applicant: National Research Council of Canada, Ottawa (CA)

(72) Inventors: Christopher Reid, Cumberland, RI (US); Susan M. Logan, Ottawa (CA); Evguenii Vinogradov, Ottawa (CA); Andrew Cox, Ottawa (CA); Jean-Robert Brisson, Ottawa (CA)

(73) Assignee: National Research Council of Canada, Ottawa (CA)

( * ) Notice: Subject to any disclaimer, the term of this patent is extended or adjusted under 35 U.S.C. 154(b) by 266 days.

(21) Appl. No.: 14/358,927

(22) PCT Filed: Nov. 16, 2012

(86) PCT No.: PCT/CA2012/001051
§ 371 (c)(1),
(2) Date: May 16, 2014

(87) PCT Pub. No.: WO2013/071409
PCT Pub. Date: May 23, 2013

(65) Prior Publication Data
US 2014/0314813 A1    Oct. 23, 2014

Related U.S. Application Data

(60) Provisional application No. 61/561,290, filed on Nov. 18, 2011.

(51) Int. Cl.
*C08B 37/00* (2006.01)
*A61K 39/08* (2006.01)
*C07H 11/04* (2006.01)
*C07H 13/02* (2006.01)
*C07H 15/04* (2006.01)
*C12Q 1/04* (2006.01)
*A61P 31/04* (2006.01)
*A61K 39/00* (2006.01)

(52) U.S. Cl.
CPC .......... *C08B 37/0024* (2013.01); *A61K 39/08* (2013.01); *A61P 31/04* (2018.01); *C07H 11/04* (2013.01); *C07H 13/02* (2013.01); *C07H 15/04* (2013.01); *C12Q 1/04* (2013.01); *A61K 2039/521* (2013.01); *A61K 2039/55566* (2013.01)

(58) Field of Classification Search
None
See application file for complete search history.

(56) References Cited

U.S. PATENT DOCUMENTS

| | | | |
|---|---|---|---|
| 5,866,132 A * | 2/1999 | Malcolm | A61K 39/092 424/193.1 |
| 6,214,341 B1 | 4/2001 | Thomas, Jr. et al. | |
| 6,248,329 B1 * | 6/2001 | Chandrashekar | C07K 14/4354 424/130.1 |
| 6,610,293 B1 | 8/2003 | Fischer et al. | |
| 6,667,035 B1 | 12/2003 | Von Eichel-Streiber et al. | |
| 6,680,168 B2 | 1/2004 | Thomas, Jr. et al. | |
| 6,733,760 B1 | 5/2004 | Wilkins et al. | |
| 6,939,543 B2 | 9/2005 | Fischer et al. | |
| 6,969,520 B2 | 11/2005 | Thomas, Jr. et al. | |
| 7,151,159 B2 | 12/2006 | Von Eichel-Streiber et al. | |
| 7,169,903 B2 | 1/2007 | Schuman et al. | |
| 7,250,494 B2 | 7/2007 | Stinson et al. | |
| 7,511,122 B2 | 3/2009 | Fischer et al. | |
| 7,608,265 B2 | 10/2009 | Burnie et al. | |
| 7,625,559 B2 | 12/2009 | Ambrosino et al. | |
| 7,777,017 B2 | 8/2010 | Stinson et al. | |
| 2002/0051793 A1 | 5/2002 | Drabick | |
| 2003/0054009 A1 | 3/2003 | Windle et al. | |
| 2003/0157133 A1 | 8/2003 | Drabick | |
| 2003/0224000 A1 | 12/2003 | Kokai-Kun et al. | |
| 2004/0013673 A1 | 1/2004 | Fischer et al. | |
| 2004/0052779 A1 | 3/2004 | Stinson et al. | |
| 2004/0247605 A1 | 12/2004 | Kokai-Kun et al. | |
| 2006/0002939 A1 | 1/2006 | Fischer et al. | |
| 2006/0029608 A1 | 2/2006 | Thomas, Jr. et al. | |
| 2006/0121058 A1 | 6/2006 | Malley et al. | |

(Continued)

FOREIGN PATENT DOCUMENTS

| | | |
|---|---|---|
| WO | WO9702835 | 1/1997 |
| WO | 9857994 | 12/1998 |

(Continued)

OTHER PUBLICATIONS

Sharp et al (FEMS Microbiology Letters, 34:97-100, 1986).*
Sanchez-Hurtado et al (Journal of Medical Microbiology, 57:739-744, 2008).*
Sharp et al, The Culture, Epidemiology and Virulence Factors of Clostridium Difficile University of Edinburgh (United Kingdom) Dissertation Abstracts International, (1987) vol. 49, No. 11B, p. 4688. Order No. AARD-84171. 326 pages.*
The Dictionary of Immunology, Herbert et al eds, Academic Press, 1995) 2 pgs.*
Feng et al (Infection and Immunity, 64(1):363-365, 1996).*
European Search Report dated Jun. 8, 2015 for corresponding European Patent Application No. 12850286.1.

(Continued)

*Primary Examiner* — Patricia Duffy
(74) *Attorney, Agent, or Firm* — Jessica Smith

(57) ABSTRACT

A novel lipoteichoic acid (LTA) was isolated from *C. difficile*, the structure of which is illustrated below wherein n is an integer between 1 and 20, R3 and R4 are independently selected from C 14:0, C 16:0, C 16:1, C 18:0 or C18:1 fatty acid or any combination thereof wherein one of COR3 or COR4 may be replaced by H. Further described are conjugates comprising the novel LTA and vaccines produced using the isolated LTA and the LTA conjugates. The invention also encompasses methods of conferring immunity against *C. difficile* comprising administering a vaccine of the invention, and methods of detecting *C. difficile* using the isolated LTA of the invention.

27 Claims, 15 Drawing Sheets

(56) References Cited

U.S. PATENT DOCUMENTS

| | | |
|---|---|---|
| 2007/0065466 A1 | 3/2007 | Windle et al. |
| 2007/0071763 A1 | 3/2007 | Burnie et al. |
| 2007/0231336 A1 | 10/2007 | Thomas, Jr. et al. |
| 2008/0014202 A1 | 1/2008 | Schuman et al. |
| 2008/0107673 A1 | 5/2008 | Ballard et al. |
| 2010/0221822 A1 | 9/2010 | Fischer et al. |
| 2010/0233181 A1 | 9/2010 | Ambrosino et al. |
| 2010/0233182 A1 | 9/2010 | Ambrosino et al. |
| 2010/0247546 A1 | 9/2010 | Fischer et al. |
| 2010/0260752 A1 | 10/2010 | Tang |
| 2011/0150907 A1* | 6/2011 | Seegers .............. A61K 31/4164 424/178.1 |

FOREIGN PATENT DOCUMENTS

| | | |
|---|---|---|
| WO | WO2009033268 | 3/2009 |
| WO | WO2009108652 | 9/2009 |
| WO | WO2010017383 | 2/2010 |
| WO | WO2010094970 | 8/2010 |
| WO | WO2010135585 | 11/2010 |
| WO | WO2012119846 | 9/2012 |

OTHER PUBLICATIONS

Cox, Andrew et al., Investigating the candidacy of a lipoteichoic acid-based glycoconjugate as a vaccine to combat Clostridium difficile infection, 2013, Glycoconjugate Journal, vol. 30, No. 9, pp. 843-855.

Hogendorf Wouter F J et al., Total synthesis of five lipoteichoic acids of Clostridium difficile, 2014, Chemistry, vol. 20 No. 42, pp. 13511-13516.

Stadelmaier A. et al., Synthesis of the first fully active lipoteichoic acid, 2003, Angewandte Chemie International Edition, vol. 42, No. 8, pp. 916-920.

Reid, CW et al., Structural characterization of surface glycans from Clostridium difficile, Carbohydr Res., 2012, vol. 354, pp. 65-73.

Antikainen J. et al., Detection of virulence genes of Clostridium difficile by multiplex PCR, APMIS 2009, 117 (8), 607-613.

Baldassarri, L., et al., Capsule-like structures in Clostridium difficile strains, Microbiologica 1991, 14 (4), 295-300.

Bauer M. P. et al, Community-onset Clostridium difficile-associated diarrhoea not associated with antibiotic usage, Neth J Med 2008, 66 (5), 207-211.

Behr et al., The structure of pneumococcal lipoteichoic acid, Eur. J Biochem. 1992, 207 (3), 1063-1075.

Albesa-Jove, David et al., Four distinct structural domains in clostridium difficile toxin B visualized using SAXS, J Mol. Biol. 2010, 396 (5), 1260-1270.

Bignardi G. E. et al., Different ribotypes in community-acquired clostridium difficile,. J Hosp Infect 2008, 70 (1), 96-98.

Burns D.A., et al., SleC is essential for germination of clostridium difficile spores in nutrient-rich medium supplemented with the bile salt taurocholate, J. Bacteriol 2010, vol. 192, 657-664.

Ciucanu I.; Kerek, F., A simple and rapid method for the permethylation of carbohydrate, Carbohydr Res 1984, 131, 209-217.

Dagan R. et al., Glycoconjugate vaccines and immune interference: A review, Vaccine, 2010, 28(34), 5513-5523.

Danieli E., et al., First synthesis of C. difficile PS-II Cell Wall Polysaccharide Repeating Unit. Organic Letters. 2011, 13 (3), 378-381.

Emerson JE, et al., A novel genetic switch controls phase variable expression of CwpV, a clostridium difficile cell wall protein, Mol Micro 2009, 74:541-556.

Fischer, W. Lipoteichoic acids and lipoglycans, Bacterial Cell Wall, Elsevier Science B.V., Amsterdam 1994. pp. 199-215.

Ganeshapillai, J. et al., Clostridium difficile cell-surface polysaccharides composed of pentaglycosyl and hexaglycolsyl phosphate repeating units, Carbohydr. Res. 2008, 343 (4), 703-710.

Grundling and Schneewind, Synthesis of glycerol phosphate lipoteichoic acid in Staphylococcus aureus, PNAS 2007, 104:8478-8483.

Henneke, P. et al, Role of lipoteichoic acid in the phagocyte response to group B Streptococcus, J Immunol. 2005, 174 (10), 6449-6455.

Huang, H. et al., Community acquired Clostridium difficile infection due to a moxifloxacin susceptible ribotype 027 strain, J Infect Dis 2009, 41 (2), 158-159.

Hussack, G., et al., Neutralization of Clostridium difficile toxin A with single-domain antibodies targeting the cell receptor binding domain, Journal of Biological Chemistry, 286 (11), pp. 8961-8976.

Jank, T. et al, Rho-glucosylating Clostridium difficile toxins A and B: new insights into structure and function, Glycobiology 2007, 17 (4), 15R-22R.

Kaier, K. et al, Relationship between Antibiotic Consumption and Clostridium difficile-Associated Diarrhea: an Epidemiological Note, Antimicrob Agents Chemother 2009, 53 (10), 4574-4575.

Kalelkar, S. et al, Structure of the capsular polysaccharide of clostridium perfringens Hobbs 5 as determined by NMR spectroscopy, Carbohydr. Res 1997, 299 (3), 119-128.

Kirby J.M. et al., Cwp84, a Surface-associated Cysteine Protease, Plays a Role in the Maturation of the Surface Layer of Clostridium difficile, J. Biol. Chem 2009, 284, 34666-34673.

Knoop, F. C. et al., Clostridium difficile: Clinical disease and diagnosis, Clin Microbiol Rev 1993, 6 (3), 251-265.

Kyne, L. et al., Health Care Costs and Mortality Associated with Nosocomial Diarrhea Due to Clostridium difficile, Clin Infect Dis 2002, 34 (3), 346-353.

Lawley TD, et al., Proteomic and Genomic Characterization of Highly Infectious Clostridium difficile 630 Spores, J. Bacteriol 2009, 191 (17), 5377-86.

Lee, L. et al., Identification of iduronic acid as a constituent of the type specific polysaccharide of clostridium perfringens Hobbs 10, Carbohydr. Res 1974a, 33 (2), 387-390.

Lee, L. et al., Capsular polysaccharide of Clostridium perfringens Hobbs 10, Infect Immun. 1974b, 9 (2), 318-322.

Young, N. M. et al., Structure of the N-Linked Glycan Present on Multiple Glycoproteins in the Gram-negative Bacterium, Campylobacter jejuni, J Biol. Chem 2002, 277 (45), 42530-42539.

Morath, S. et al., Structural Decomposition and Heterogeneity of Commercial Lipoteichoic Acid Preparations, Infect Immun. 2002, 70 (2), 938-944.

Oberli, M.A., et al., A possible oligosaccharide-conjugate vaccine candidate for clostridium difficile is antigenic and immunogenic, Chem Biol, 2011, 18 (5), 580-588.

Paine, C. et al., Composition of the capsular polysaccharides of Clostridium perfringens as a basis for their classification by chemotypes, J Microbiol 1975, 21 (2), 181-185.

Perez J, et al., Clospore: a liquid medium for producing high titers of semi-purified spores of Clostridium difficile, 2011, J. AOAC Int 94, 618-26.

Pituch, H., Clostridium difficile is no longer just a nosocomial infection or an infection of adults, Int J Antimicrob Agents 2009, 33 Suppl 1, S42-S45.

Pokorn, M. et al., Severe clostridium difficile-associated disease in children, Pediatr Infect Dis J 2008, 27 (10), 944-946.

Poxton, I.R. et al., Immunochemistry of the Cell-Surface Carbohydrate Antigens of Clostridium difficile, J. Gen Micro 1982, 128, 1365-1370.

Read S. M., Analysis of the structural heterogeneity of laminarin by electrospray-ionisation-mass spectrometry, Carbohydr Res 1996, 281 (2), 187-201.

Songer, J. G., et al., Clostridium difficile in Retail Meat Products, USA, 2007, Emerg. Infect Dis 2009, 15 (5), 819-821.

St. Michael, F. et al., The structures of the lipooligosaccharide and capsule polysaccharide of campylobacter jejuni genome sequenced strain NCTC 11168, Eur. J Biochem. 2002, 269 (21), 5119-5136.

Storz, C. A. et al., Polysaccharides from Peptostreptococcus anaerobius and structure of the species-specific antigen, J. Carbohydrate Res. 1990, 207, 101-120.

Twine, S. et al., Motility and Flagellar Glycosylation in Clostridium difficile, J Bacteriol. 2009, 191 (22), 7050-7062.

Weese, J. S. et al, Detection and Enumeration of Clostridium difficile Spores in Retail Beef and Pork, J. Appl. Environ. Microbiol 2009, 75 (15), 5009-5011.

(56) References Cited

OTHER PUBLICATIONS

Weese, J. S., et al., Detection and characterization of Clostridium difficile in retail chicken, Lett. Appl. Microbiol 2010, 50 (4) 362-365.
Wilkins, T. D. et al., Clostridium difficile Testing: after 20 Years, Still Challenging, Clin Microbiol 2003, 41 (2), 531-534.
International Search Report and Written Opinion for corresponding PCT Application No. PCT/CA2012/001051.

* cited by examiner

CLOSTRIDIUM DIFFICILE LIPOTEICHOIC ACID AND USES THEREOF

CROSS-REFERENCE TO RELATED APPLICATIONS

This application is a national phase entry of International Patent Application No. PCT/CA2012/001051 filed Nov. 16, 2012 and claims the benefit of United States Provisional patent application U.S. Ser. No. 61/561,290 filed Nov. 18, 2011, the entire contents of which is hereby incorporated by reference.

FIELD OF THE INVENTION

The present invention relates to a lipoteichoic acid (LTA) and uses thereof. More specifically, the invention relates to a *Clostridium difficile* lipoteichoic acid and its use as a vaccine to combat *Clostridium difficile* and as a diagnostic antigen.

BACKGROUND OF THE INVENTION

*Clostridium difficile* is a Gram-positive anaerobe that is the cause of enteric disease in many animal species including humans. In humans, *C. difficile* associated diarrhea (CDAD) is a commonly diagnosed cause of hospital-associated and antimicrobial-associated diarrhea. With the emergence of the hypervirulent NAP1/027 strains in hospitals globally, a sharp increase in mortality rates has been observed (Kaier and Frank, Antimicrob Agents Chemother 2009, 53 (10), 4574-4575). While previous reports of *C. difficile* epidemics were restricted to single institutions or wards, more recently reports of a wider distribution of outbreaks are increasing (Bignardi et al, J Hosp Infect 2008, 70 (1), 96-98). Infection with *C. difficile* can lead to severe diarrhea, abdominal pain and further complications such as pseudomembranous colitis, inflammation and ulceration of the lining of the intestinal wall.

Current practice for the treatment of CDAD is the administration of antibiotics. Metronidazole, vancomycin, and fidaxomicin are among the most commonly-used antibiotics for treatment of CDAD. However, these approaches can only be used once the patient has contracted CDAD, and may be inefficient in the face of a drug-resistant bacterium. Additionally, the relapse rate of successfully treated patients is approximately 20%.

In light of the emergence and increasing severity of CDAD, there has been a significant increase in the number of research articles on *C. difficile* detection and characterization of virulence factors and toxins. However, to date little attention has been paid to the surface carbohydrate-containing molecules produced by this emerging pathogen. An early study by Poxton and Cartmill, J. Gen Micro 1982, 128, 1365-1370, described the characterization of two cell surface antigens extracted from the bacterial cell surface. Twenty years ago, the identification of a capsular polysaccharide (CPS)-like structure by electron microscopy was reported (Baldassarri et al, Microbiologica 1991, 14 (4), 295-300) followed by a detailed characterization of a *C. difficile* CPS (Ganeshapillai et al, Carbohydr. Res. 2008, 343 (4), 703-710). A recent publication demonstrated that the flagellin protein from a number of *C. difficile* clinical isolates was glycosylated with a novel O-linked glycan (Twine et al, 2009, 191(22), 7050-7062). In general however, the surface polysaccharides of the genus *Clostridium* are relatively poorly understood. Although there is information relating to *C. perfringens* CPS structures (Kalelkar et al, 1997, 299 (3), 119-128), the *Clostridium* genus is diverse genetically and it is unlikely that surface polysaccharides are conserved across the genus.

With respect to CPS of *C. difficile*, the work of Ganeshapillai, supra showed that a ribotype 027 strain produced two polysaccharides; the first polysaccharide (PSI) was a branched pentaglycosyl phosphate repeat unit composed of [→4-α-L-Rhap-(1→3)-β-D-Glcp-(1→4)-[α-L-Rhap-(1→3]-α-D-Glcp-(1→2)-α-D-Glcp-(1→P→] while the second polysaccharide (PSII) consisted of a hexaglycosyl phosphate repeat unit with the structure [→6)-β-D-Glcp-(1→3)-β-D-GalpNAc-(1→4)-α-D-Glcp-(1→4)-[β-D-Glcp(1→3]-β-D-GalpNAc-(1→3)-α-D-Manp-(1→P→]. The authors also confirmed the presence of the latter structure on the surface of two other *C. difficile* isolates; however, they also acknowledged that further investigations regarding the use of the structures in immune response were warranted.

Others (Oberli et al, Chem Biol, 2011, 18 (5), 580-588; Danieli et al, Org Letters. 2011, 13 (3), 378-381; Monteiro et al, WO 2009/033268) have-investigated vaccines that target the PSII CPS. Oberli, supra, and Danieli, supra, both use a synthetic monomeric structure to target the CPS; however, this may not provide a good mimic of the natural epitopes present on the polymers on the pathogen. Monteiro shows limited cross-reactivity of the PSII polysaccharide. To date, no further vaccines have been reported against *C. difficile* surface polysaccharides.

Another strategy is a therapeutic approach against the *C. difficile* toxin. This involves the use of antibodies (e.g., monoclonal antibodies) or antibody fragments (e.g., single-domain antibodies) specific for the toxin (for example, Hussack et al, 2011 JBC 286 (11), pp. 8961-8976). However, this anti-toxin strategy does not kill the bacteria, but rather only neutralizes the toxin, leaving the bacteria intact.

Thus, it is clear to those of skill in the art that there remains a profound need to establish a conserved and broadly cross-reactive, immunogenic antigen in order to develop a safe and effective vaccines for conferring immunity to patients at risk for developing *C. difficile* infections.

SUMMARY OF THE INVENTIO

The present invention relates to a lipoteichoic acid (LTA) and uses thereof. More specifically, the invention relates a *Clostridium difficile* lipoteichoic acid and its use as a vaccine to combat *Clostridium difficile*.

The present invention provides an isolated LTA comprising a structure of Formula I

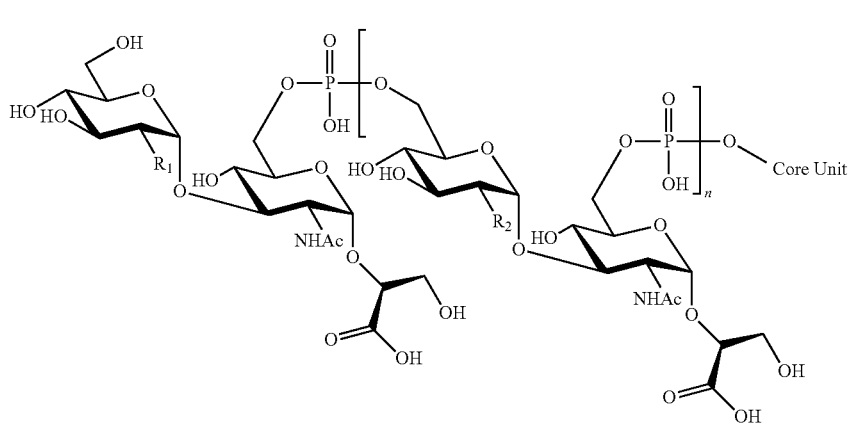

I wherein $R_1$ is selected from $NH_2$ and NHAc; each $R_2$ is independently selected from $NH_2$ and NHAc; and n is an integer between about 1 and 20. In a preferred embodiment, n is 12-16. The isolated LTA may have a degree of acetylation of the LTA in the range of about 65 to 100%. In a preferred embodiment, the degree of acetylation may be in the range of 65-75% or of about 70%. The isolated LTA of the invention may have a percentage of de-acetylation in the LTA between about 25 and 35%, or of about 30%.

In the LTA as described above, the carbohydrate residues may be further substituted by D-alanine (D-ala), phosphorylcholine, or by other sugars such as glucose, galactose, N-acetylglucosamine, N-acetylgalactosamine and ribitol (Weidenmaier & Peschel, Nat. Rev. Microbiol. 2008 v6 p 276-287).

The core unit of the isolated LTA of the present invention may comprise three glucose (Glcp) residues and a glycerol (Gro) residue. The Gro residue of the core unit may be esterified by one or more than one fatty acid. In a preferred embodiment, the Gro residue is esterified by two fatty acids. In one non-limiting example, the core unit may comprise the structure of Formula II

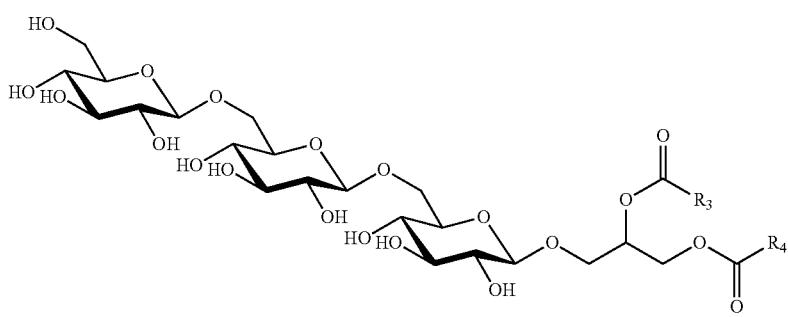

II wherein at least one of $R_3$ and $R_4$ is independently selected from a C14:0, C:16:0 C16:1 C18:0, or C18:1 fatty acid, or any combination thereof. In embodiments wherein the Gro residue of the core unit is esterified by only one fatty acid, one of $COR_3$ or $COR_4$ is replaced by H.

In one embodiment of the invention, the isolated LTA of the present invention may comprise the structure of Formula III of suitable carrier molecules include flagellin, human serum albumin (HSA), tetanus toxoid (TT), diphtheria toxoid (CRM or DT), Exotoxoid A, protein D, cholera toxin B subunit.

The present invention also encompasses a *C. difficile* vaccine comprising one or more than one isolated LTA as described herein. The *C. difficile* vaccine may further comprise an adjuvant. Examples of suitable adjuvants include

III

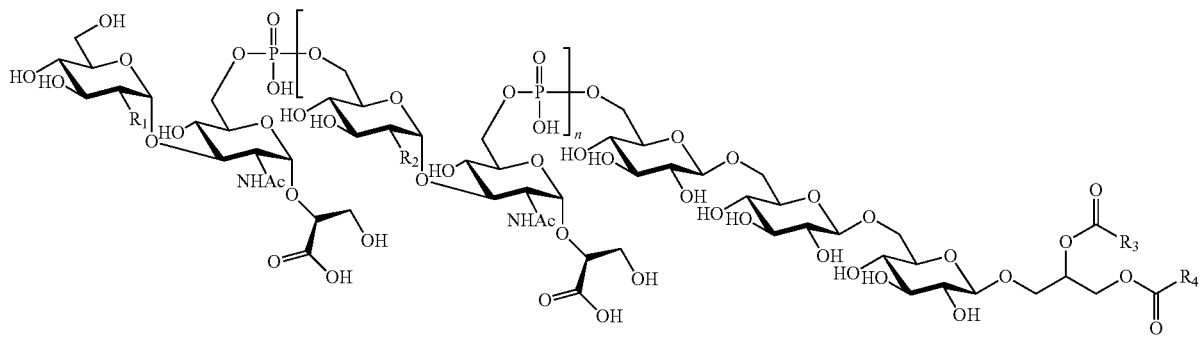

wherein $R_1$ is selected from $NH_2$ and NHAc; each $R_2$ is independently selected from $NH_2$ and NHAc; n is an integer between about 1 and 20; and at least one of $R_3$ and $R_4$ is independently selected from a C14:0, C:16:0 C16:1 C18:0 or C18:1 fatty acid, or any combination thereof. In embodiments wherein the Gro residue of the core unit is esterified by only one fatty acid, one of $COR_3$ or $COR_4$ is replaced by H. In a preferred embodiment, n is 12-16.

In another specific, non-limiting example of the invention, the isolated LTA of the present invention may comprise the structure of Formula IV.

attenuated viral and bacterial vectors and the AMVAD adjuvant (Patel et al, 2007 Vaccine 25: 8622-8636).

The present invention also provides a composition comprising the isolated LTA as described herein and a pharmaceutically acceptable diluent, carrier, or excipient.

The present invention further provides a method of conferring immunity against *C. difficile* comprising administering an effective amount of the isolated LTA, the *C. difficile* vaccine, or the composition as described herein to a subject in need thereof.

IV

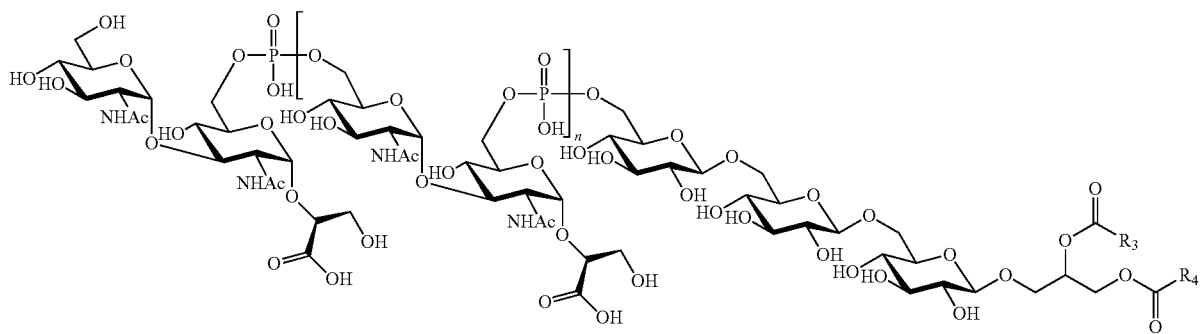

wherein n is an integer between 1 and 20 and at least one of $R_3$ and $R_4$ is independently selected from a C14:0, C:16:0 C16:1 C18:0 or C18:1 fatty acid, or any combination thereof. In embodiments wherein the Gro residue of the core unit is esterified by only one fatty acid, one of $COR_3$ or $COR_4$ is replaced by H. In a preferred embodiment, n is 12-16.

The isolated LTA as described herein may be linked to a carrier molecule. The carrier molecule may be selected from the group consisting of a peptide, a protein, a membrane protein, a carbohydrate moiety, or one or more liposomes loaded with any of the previous carrier molecules. Examples The present invention further provides a method of detecting the presence of *C. difficile* using the isolated LTA described herein.

Additional aspects and advantages of the present invention will be apparent in view of the following description. The detailed description and examples, while indicating preferred embodiments of the invention, are given by way of illustration only, as various changes and modifications within the scope of the invention will become apparent to those skilled in the art in light of the teachings of this invention.

BRIEF DESCRIPTION OF THE DRAWINGS

These and other features of the invention will now be described by way of example, with reference to the appended drawings, wherein:

FIG. 5A shows the extracted MS/MS spectrum of precursor ions at m/z 858.0, while FIG. 5B shows the extracted MS/MS spectrum of precursor ions at m/z 696.0. The precursor ions were generated by increasing the orifice voltage to +350 V. $N_2$ as collision gas; 40 eV (laboratory frame reference).

DETAILED DESCRIPTION OF THE INVENTION

The present invention relates to a lipoteichoic acid (LTA) and uses thereof. More specifically, the invention relates to a *Clostridium difficile* LTA and its use as a vaccine to combat *Clostridium difficile*.

Lipoteichoic acids are often zwitterionic cell wall polymers most commonly composed of polyglycerol phosphate chains linked to a glycolipid anchor found on the surface of Gram positive bacteria. They are a major constituent of the cell wall of Gram-positive bacteria. While the exact function of teichoic acid is currently not clear, it has been shown that absence of LTA causes severe morphological defects, resulting in bacteria that are only viable under certain growth conditions (Grundling & Schneewind, PNAS 2007, 104: 8478-8483). The structure of LTA varies significantly between different classes and species of bacteria. In particular, LTA is known to vary in the length of the chains and the location and type of substituents. Substituents can include amino acids, sugars such as D-glucose, and amino sugars such as N-acetyl-D-glucosamine and N-acetyl-D-galactosamine.

In US 2006/0002939, mice immunized with whole strain *Staphylococcus epidermidis* produced a wide range of antibodies some of which bound to commercially purchased LTA. However, the structure of the LTA was not known.

The inventors of the present application have isolated and characterized a novel LTA from *C. difficile*. The inventors cultured 39 different strains of *C. difficile* (see Table 1). Of these 39 strains, the following 11 strains were subjected to a survey of surface carbohydrate diversity using whole-cell high resolution magic angle spinning (HR-MAS) NMR:
  630, BI-7, BI-1, QCD32g58, CM26, CM56, 06Cd-130, 955289, D0835450, D0503439 and D0632920.

Of the 11 strains surveyed, including genome-sequenced strain 630 and a clinical isolate from an outbreak in Manitoba, Canada in 2000 (CM-26), a highly conserved anomeric region was observed.

Figure 2A:
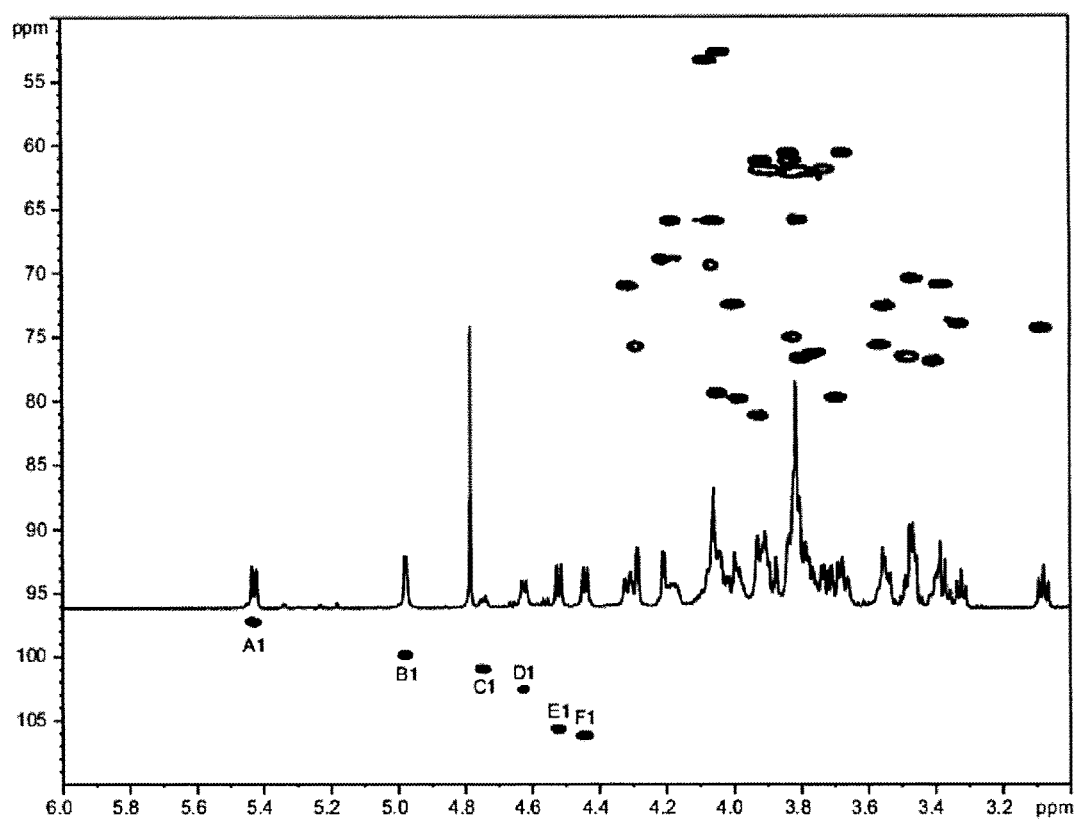
FIG. 2A shows the NMR spectra of PS-II for *C. difficile* CM-26. The proton spectrum and $^1$H-$^{13}$C HSQC correlation spectrum with the anomeric resonances labelled A-F show the presence of PS-II shown in FIG. 3.

Following hot water extraction of the cells and one and two-dimensional NMR experiments, a non-lipidated polysaccharide (PS-II) was confirmed to be identical to the hexaglycosyl phosphate repeating block of [→6)-β-Glc-(1→3)-β-GalNAc-(1→4)-α-Glc-(1→4)-[β-Glc(1→3]-β-GalNAc-(1→3)-α-Man-(1→P→] (PSII) reported previously (FIG. 2A).

A second, novel, conserved glycan polymer, was also observed in the 11 strains. This glycan polymer, an LTA, was isolated following a phenol extraction from strains 630, VPI10463 and CM-26. The LTA was lipid-linked either to $C_{14}$, $C_{16}$, or $C_{18}$, saturated or mono-unsaturated fatty acids. It was also visible by HR-MAS NMR (FIG. 1) indicating that it is a major conserved component of the cell surface carbohydrates. A complete structural analysis was performed on the novel LTA, which enabled determination of its structure. The LTA described herein comprises a repeating unit –[6-α-GlcNAc(1→3'-α-GlcNAc-((1→2)-GroA)-6→P→]) that is connected to a lipid anchor via a core unit.

The predominant component of the LTA was an α-linked GlcNAc-GlcNAc-glyceric acid repeating unit linked through a 6-6 phosphodiester bridge between C-6 of the two GlcNAc residues (6-P-6). This portion of the structure was previously found in cell-envelope polysaccharide antigens of the Gram-positive organism, *Peptostreptococcus anaerobius* following extraction from intact cells by autoclave or alkaline treatment (Storz et al, J. Carbohydrate Res. 1990, 207, 101-120). However, the entire structure of the novel LTA has never been previously reported. The inventors of the presently claimed invention have identified, in addition to the repeat unit, the terminal residue and the core unit (see FIG. 3). A minor component of the LTA from *C. difficile* comprising approximately 30% GlcN-GlcNAc-GroA in place of GlcNAc-GlcNAc-GroA was also observed. The core unit contained the β-linked Glc-Glc-Glc-Gro with glycerol esterified by fatty acids.

The LTA identified herein is quite distinct to the reported structures of LTA from other Gram-positive organisms within the Phylum Firmicutes (low GC). However, the structural studies completed to date on LTAs have primarily focused on organisms from the class Bacilli within this Phylum (Henneke et al, J Immunol. 2005, 174 (10), 6449-6455; Morath et al 2002, 70 (2), 938-944; Behr et al, Eur. J Biochem. 1992, 207 (3), 1063-1075; Han et al., Infect Immun. 2003 October; 71(10):5541-8 (e.g. *Bacillus, Streptococcus, Staphylococcus, Lactobacillus, Staphylococcus* spp) while the present invention focuses on an LTA from *C. difficile*, which is a member of the class Clostridia. A previous report on *C. innocuum* had demonstrated that the LTA contained a Gal-Gro-P repeating unit (Fischer, Bacterial Cell Wall Ghuysen and Hakenbeck (eds) Elsevier Science B.V. 1994,) which is different from the repeating unit of the LTA of the present invention. Given that the LTA was present in all 11 tested strains, and based on immunological studies reported further herein, the inventors of the present application have determined that the distinct structure of the LTA is representative of the *C. difficile* species.

The present invention provides an isolated LTA comprising a structure of Formula I wherein $R_1$ is selected from $NH_2$ and NHAc; each $R_2$ within the repeating unit is independently selected from $NH_2$ and NHAc; and n is an integer between about 1 and 20. In a preferred embodiment, n is 12-16. The entire polymer may have a degree of acetylation in the range of about 60-100%, preferably 65-75% or about 70%, due to acetylation of the combination of $R_1$ and $R_2$.

Figure 3:
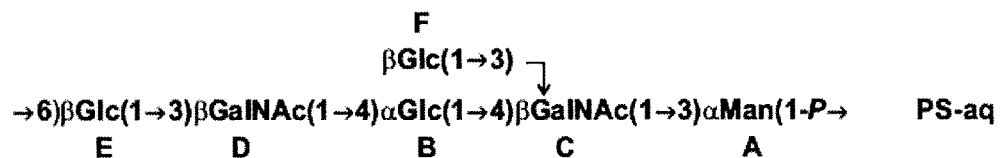
FIG. 3 shows the capsule and lipoteichoic acid structures observed from *C. difficile* 630 and CM-26 strains. Residues are labelled according to the assignment of the resonances in FIGS. 1 and 2 and the NMR data in Table 2. For the O-deacylated LTA a minor component (30%) consisted of aGlcpN(1-*3) instead of aGlcpNAc-(1-3) in the repeat unit.
Figure 3:
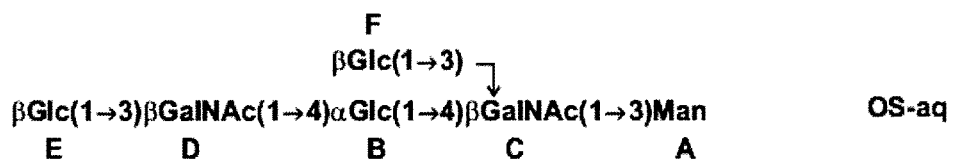
Figure 3:
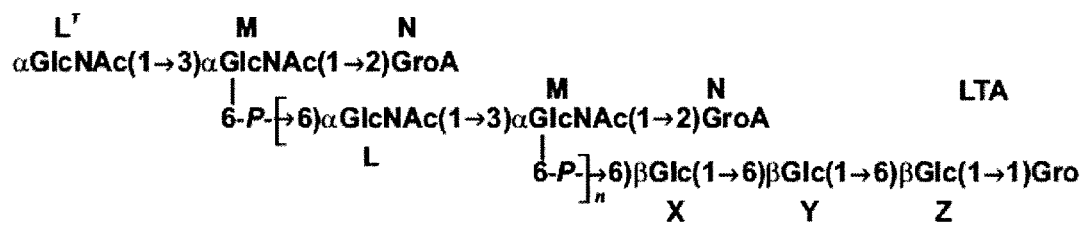
Figure 3:
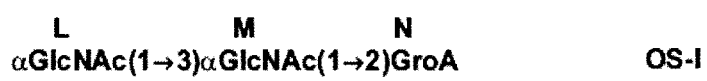
Figure 3:
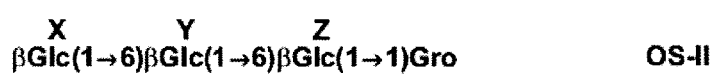

In the repeating unit, as described above, n is an integer between about 1 and 20. For example, and without wishing to be limiting in any manner, n may be about 1, 2, 3, 4, 5, 6, 7, 8, 9, 10, 11, 12, 13, 14, 15, 16, 17, 18, 19, or 20. In a non-limiting example, n may be about 12 to 16. Thus, the molecular weight of the LTA as described above will vary based on the value of n. For example, and without wishing to be limiting in any manner, the molecular weight of the LTA may be between about 5 and 10 kDa. In a non-limiting example, the molecular weight of the LTA may be about 8-12 kDa. For example, the OS-I repeating unit may be as shown in FIG. 3, where the residues are labelled L-M-N.

The repeating unit may be capped by a terminal unit. The terminal unit in the LTA as described herein and shown in Formula I is noted as $L^T$-M-N, which is the same as the repeating unit, except that a terminal GlcpNAc or GlcN is present. For example, the terminal unit may be as shown in FIG. 3, where the residues are labelled $L^T$-M-N.

As described above, each $R_2$ within the repeating unit of the isolated LTA of the present invention may be the same or different. For example, and strictly for the purpose of illustration, when n=3, each of the three $R_2$ of the repeating unit is independently selected from $NH_2$ and NHAc. Thus, in this illustration, the repeating unit may comprise 0, 1, 2,

I

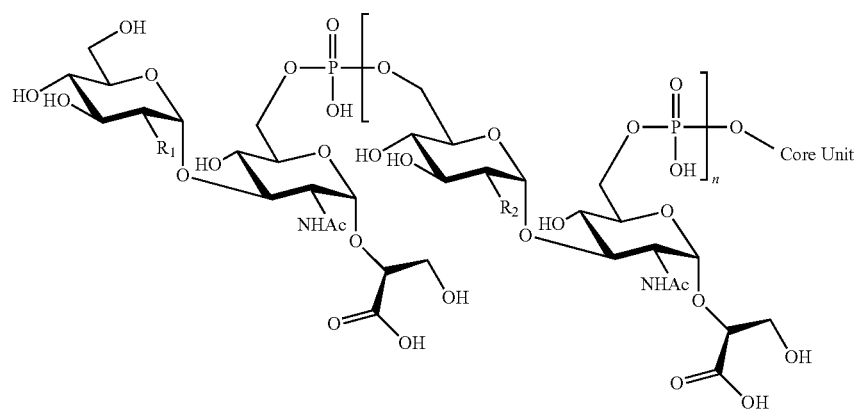

which may, alternatively, be written as follows:

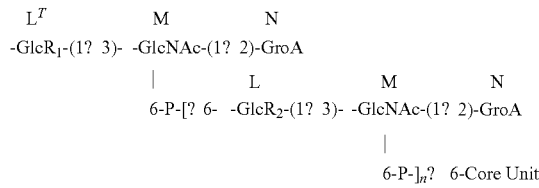

or 3 $NH_2$ at position $R_2$. Similarly, $R_1$ of the terminal unit of the isolated LTA of the present invention is selected independently from $R_2$ and may be the same as or different from any given $R_2$.

The selection of the $R_1$ and $R_2$ groups results in a degree of acetylation of the LTA polymer. By "degree of acetylation", it is meant the percentage of LTA that comprises NHAc at the $R_1$ and $R_2$ positions combined. This degree of acetylation may be between about 60% and 90%, or between about 65% and 75%; for example, the degree of acetylation may be about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90%, or any value in between. In one non-limiting example, the proportion of GlcNAc in the LTA may be approximately 70%.

Stated alternatively, the degree of deacetylation in the LTA may be between about 10% and 40%, or between about 25% and 35%; for example, the proportion of GlcN may be about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40%, or any value therein between. By "degree of deacetylation", it is meant the percentage of LTA that comprises NH at the $R_1$ and $R_2$ positions combined. In one non-limiting example, the degree of deacetylation (i.e., GlcN) in the LTA may be approximately 30%.

In the LTA of the present invention, the residues within the repeating and terminal units may be further substituted. For example, and without wishing to be limiting, the residues may be further substituted by D-alanine (D-Ala), phosphorylcholine, or by sugars such as D-glucose or amino sugars such as N-acetyl-D-glucosamine. This type of substitution is well-known to those of skill in the art (see, for example, Ghuysen, J. M., Bacterial Cell Wall (Elsevier Science B.V., 1994, Amsterdam at page 201). The repeating unit is also connected to a core unit. The core unit may be a glucose trisaccharide, which may link the repeating unit to a lipid anchor. Such a core unit of the isolated LTA described herein may comprise three glucose (Glcp) residues and a glycerol (Gro) residue. Structures of Glcp and Gro residues are well-known to those of skill in the art. In one specific example, the glucose trisaccharide of the isolated LTA may comprise the structure of Formula II

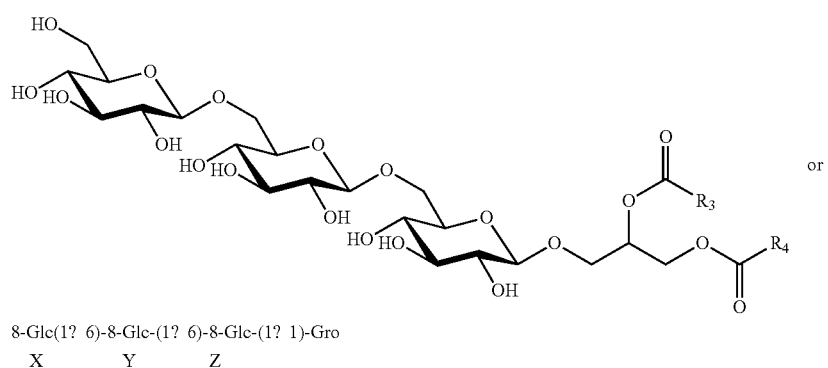

II

8-Glc(1? 6)-8-Glc-(1? 6)-8-Glc-(1? 1)-Gro
   X          Y          Z as shown in FIG. 3, where the carbohydrate residues are labelled X-Y-Z. The core unit may have a molecular weight of approximately 500 Da.

The Gro residue of the core unit as described above may be esterified by one or more than one fatty acid. It is known that many different fatty acids are found in *Clostridium* (Elsden et al, 1980, J. Gen Microbio. 1980: 115-123). In one example, the Gro residue is esterified by two fatty acids. By the expression, "one or more than one fatty acid", it is meant that the fatty acid may be a single type of fatty acid, or a mixture of fatty acids; for example, and without wishing to be limiting in any manner, at least one of $R_3$ and $R_4$ in the structure of Formula II above is independently selected from a C14:0, C:16:0, C16:1, C18:0 or C18:1 fatty acid, or any combination thereof. In embodiments wherein the Gro residue of the core unit is esterified by only one fatty acid, one of $COR_3$ or $COR_4$ is replaced by H.

By the term "connected", also referred to herein as "linked", it is meant that the repeating unit is covalently linked to the core unit. The covalent linkage may be a direct covalent linkage between residues or may be via a functional group, for example but not limited to a phosphodiester bridge. A phosphodiester bridge (or bond) joins the carbons of two carbohydrate residues to a phosphate group over two ester bonds.

In one specific, non-limiting example, the LTA of the present invention may comprise the structure of Formula III

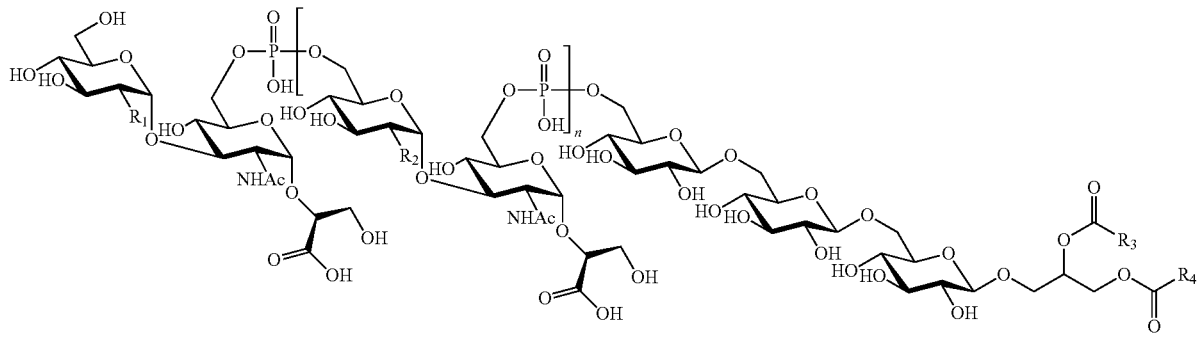

III

Or, the structure of Formula III may be written as follows:

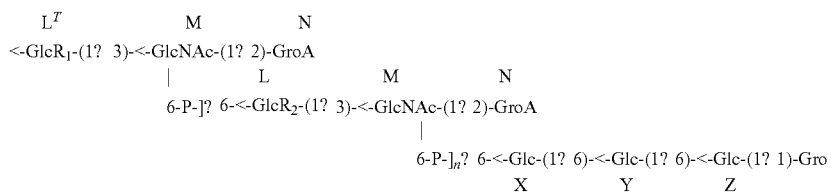

wherein $R_1$ is selected from $NH_2$ and NHAc; each $R_2$ within the repeating unit is independently selected from $NH_2$ and NHAc; n is an integer between 1 and 20; and at least one of $R_3$ and $R_4$ is independently selected from a C14:0, C:16:0 C16:1 C18:0 or C18:1 fatty acid, or any combination thereof. In embodiments wherein the Gro residue of the core unit is esterified by only one fatty acid, one of $COR_3$ or $COR_4$ is replaced by H. The entire polymer may have a degree of acetylation in the range of about 60-100%, or between about 65% and 75%, or about 70% due to acetylation of the combination of $R_1$ and $R_2$. Individual features of the LTA are as described herein.

The present invention also encompasses embodiments wherein all $R_1$ and $R_2$ within a LTA polymer are NHAc, as well as LTA polymers wherein all $R_1$ and $R_2$ are $NH_2$. In one specific, non-limiting example, the isolated LTA of the present invention may be as shown in FIG. 3, where it is labelled "LTA".

In a specific, non-limiting example of the invention, the isolated LTA of the present invention may comprise the structure of Formula IV.

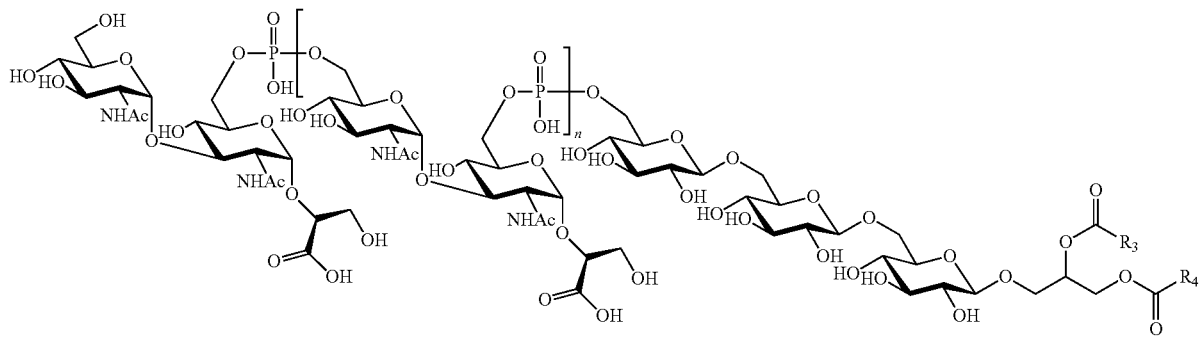

IV wherein n is an integer between 1 and 20 and at least one of $R_3$ and $R_4$ is independently selected from a C14:0, C:16:0 C16:1 C18:0 or C18:1 fatty acid, or any combination thereof. In embodiments wherein the Gro residue of the core unit is esterified by only one fatty acid, one of $COR_3$ or $COR_4$ is replaced by H. In a preferred embodiment, n is 12-16.

The LTA as described herein may be obtained by any suitable method. For example, the LTA may be natural, obtained by isolation from *C. difficile* strain(s), or may be synthesized using methods known to those of skill in the art (Kusumoto et al, 1996, J Synth Org Chem Jpn 54: 976-987; Marcus et al, Angew. Chem. Int. Ed 2010 49:2585-2590; Stadelmaier et al, Angew. Chem. Int. Ed. 2003 42: 916-920).

The present invention further encompasses conjugates comprising the isolated LTA described herein. The conjugates may comprise the novel LTA as described above linked to a carrier molecule. The carrier molecule may be any suitable molecule known in the art. For example, and without wishing to be limiting in any manner, the carrier molecule may be a peptide, a protein, a membrane protein, a carbohydrate moiety, or one or more liposomes loaded with any of the previously recited types of carrier molecules or with the LTA itself. For example, and without wishing to be limiting in any manner, the carrier molecule may be flagellin, human serum albumin (HSA), tetanus toxin (TT), diphtheria toxoid (CRM or DT), exotoxin A, protein D, cholera toxin B subunit, or other suitable carrier protein/peptide (for example see Dagan et al, Vaccine, 2010, 28(34), 5513-5523 for a review of suitable carrier molecules). In a further non-limiting example, the carrier molecule may be a liposome, for example an archaeosome (Krishnan et al, Infect and 1 mm: 2000 68 54-63), loaded with any of the molecules noted above; this renders the construct well-suited as a delivery agent for mucosal vaccines. The carrier molecule may be linked to the LTA by any suitable method known in the art. For example, and without wishing to be limiting, the carrier molecule may be linked to the LTA by a covalent bond or ionic interaction, either directly or via a linker. The linkage may be achieved through a chemical cross-linking reaction, for example a thiol linkage. The carrier protein may be conjugated to the LTA as described above via any suitable group; for example and without wishing to be limiting in any manner, the carrier protein may be conjugated to a GlcN residue at position L, resulting from $R_1$ and/or $R_2=NH_2$ within the structure. Methods for linking LTA to a carrier molecule would be well-known to a person of skill in the art (Cox et al, 2010 Glycoconj J. 27: 401-407). Methods of preparing glycoconjugate vaccines are well described in the prior art and these methods are widely known and practiced by those of skill in the art (see, for example Pace, D, 2012, Exp Opin Biol Ther. EPub Ahead of Print, Sep. 20, 2012.

The present invention also provides compositions or formulations comprising the compounds described herein, including the isolated LTA described herein and/or conjugates comprising the isolated LTA. Additionally, the present invention provides a *C. difficile* vaccine comprising the isolated LTA described herein and/or conjugates comprising the isolated LTA as described herein.

The inventors of the present application have found that the vaccines of the present invention produce sera in mammals which are reactive with each of the 39 strains of *C. difficile* cultured. Accordingly, the vaccines of the present invention are effective against the entire *C. difficile* species.

The inventors of the present application have also found that, unlike many isolated carbohydrate compounds, the isolated LTA of the present invention is an effective immunological agent which produces an IgG response (see Table 7). An IgG response has significant prophylactic benefit since the host will retain antibodies in its system and be able to mount an immunological response against subsequent exposure to the pathogen. Accordingly, while the production of a conjugate may provide enhanced immunogenicity, it is possible to produce an effective vaccine using isolated LTA alone. This feature of the present invention has benefit for vaccine manufacturers, who may find enhanced efficiency in using the isolated LTA without conjugation.

The vaccines of the present invention demonstrated high titres when administered to mice and rabbits, indicating that vaccines of the invention are useful against *C. difficile*.

The compositions, formulations, or vaccines may further comprise pharmaceutically acceptable diluents, carriers, or excipients. By the term "pharmaceutically acceptable", it is meant that the diluent, carrier, or excipient is compatible with the compound of the present invention, and is not deleterious to the recipient of the composition.

The diluent, carrier, or excipient may be any suitable diluent, carrier, or excipient known in the art, and must be compatible with other ingredients in the composition and with the method of delivery of the compositions, formulations, or vaccines. The composition may be in any suitable form; for example, the compositions, formulations, or vaccines may be provided in suspension form, powder form (for example, but not limited to lyophilised or encapsulated), capsule or tablet form. For example, and without wishing to be limiting, when the compositions, formulations, or vaccines are provided in suspension form, the carrier may comprise water, saline, a suitable buffer, or additives to improve solubility and/or stability; reconstitution to produce the suspension is effected in a buffer at a suitable pH to ensure the viability of the antibody or fragment thereof. Dry powders may also include additives to improve stability and/or carriers to increase bulk/volume; for example, and without wishing to be limiting, the dry powder composition may comprise sucrose or trehalose. In a specific, non-limiting example, the compositions, formulations, or vaccines may be so formulated as to deliver the LTA to the gastrointestinal tract of the subject. Thus, the compositions, formulations, or vaccines may comprise encapsulation, time-release, or other suitable technologies for delivery of the LTA. It would be within the competency of a person of skill in the art to prepare suitable compositions, formulations, or vaccines comprising the present compounds (see, for example, Rappuoli, R. And Bagnoli, F. eds, Vaccine Design, Innovative Approaches and Novel Strategies, (Caister Academic Press: 2011, Norfolk UK).

The composition, formulation, or vaccine as described above may also comprise an adjuvant. The adjuvant may increase the specificity of the immune response, or may increase the level of immune response. In some instances, the adjuvant may be the carrier molecule (for example but not limited to cholera toxin B subunit, liposome, etc); in other instances, the adjuvant may be an unrelated molecule known to increase the response of the immune system (for example but not limited to attenuated bacterial or viral vectors, AMVAD (Patel et al, 2007, Vaccine, 25: 8622-8636). Other suitable adjuvants are well-known to those of skill in the art. In one example, the adjuvant may be an adjuvant/carrier protein that generates a strong mucosal immune response such as an attenuated virus or bacteria, or aluminum salts. Another suitable adjuvant is known as MF59, which contains 2,6,10,15,19,23-Hexamethyltetracosa-2,6,10,14,18,22-hexaene, also known as squalene, which can be obtained from shark liver oil or certain plant sources.

The present invention also provides a method of conferring immunity against *C. difficile* comprising administering an effective amount of the isolated LTA of the present invention or a composition comprising the isolated LTA, or a conjugate comprising the LTA of the present invention to a subject in need thereof. Any suitable method of delivery may be used. For example, and without wishing to be limiting in any manner, the LTA or the composition of the present invention may be delivered enterally or parentally (orally, nasally, rectally intravenously, subcutaneous, intraperitoneally, transdermally, etc.). For example, and without wishing to be limiting, the LTA or composition of the present invention may be delivered via a route that achieves a strong mucosal immune response. Those of skill in the art would be familiar with such methods of delivery. Accordingly, the LTA of the present invention and as described above can be used to confer immunity against *C. difficile*, or could be used to prepare a medicament for conferring immunity against *C. difficile*.

Sera produced by rabbits administered whole cells of *C. difficile* was shown to comprise antibodies, of which a large portion were antibodies to LTA. This sera was also shown to be opsonic, or exhibit opsonic activity, for *C. difficile*. More specifically, these sera promote attachment of the *C. difficile* to a phagocyte and thereby enhance phagocytosis, which results in death of the *C. difficile* cells. Opsonic activity is a measure of the ability of sera to kill cells and therefore provides a measure of the ability of a vaccine to generate an immunogenic response with is lethal to the pathogen.

The present invention will be further illustrated in the following examples. However, it is to be understood that these examples are for illustrative purposes only and should not be used to limit the scope of the present invention in any manner.

Example 1: Cell Culture

The *C. difficile* isolates examined herein are shown in Table 1. All strains are from distinct outbreaks and display unique typing profiles. Isolates were grown on brain heart infusion (BHI) broth and solid media supplemented with 0.5 g $L^{-1}$ cysteine-HCl, 5 mg $L^{-1}$ hemin, 1 mg $L^{-1}$ vitamin $K_1$, and 1 mg $L^{-1}$ resazurin. Bacteria were grown under anaerobic conditions in a miniMACs workstation (Microbiology International, Frederick, Md.) at 37° C.

TABLE 1

*C. difficile* strains.

| *C. difficile* strain | Characteristics |
|---|---|
| 630 | $A^+$, $B^+$, Epidemic type X, ribotype 012, Zurich, 1982 |
| BI-1 | Fluoroquinone sensitive, toxinotype 2, non-epidemic, Minneapolis, MN, 1988 |
| BI-7 | Fluoroquinone resistant, toxinotype 3, epidemic, Portland, OR, 2003 |
| CM-26 | $A^+$ $B^+$, Manitoba, Canada, (44 cases) 2000 |
| CM-56 | $A^+$ $B^+$, Manitoba, Canada, (20 cases) 2000 |
| 06Cd-130 | $A^+$ $B^+$, Manitoba, Canada, (6 cases) 2006 |
| QCD32g58 | BI/NAP1/027, Quebec, Canada 2004 |
| 955289 | $A^+$ $B^+$, $CdtB^+$ |
| D0835450 | $A^+$ $B^+$, $CdtB^-$, intestinal swab, swine, Prairie Diagnostic Services, Saskatoon, SK |
| D0632920 | $A^-$ $B^-$ $CdtB^-$, mesocolon isolate, swine, Prairie Diagnostic Services, Saskatoon, SK. |
| D0724491 | Porcine colon isolate, Prairie Diagnostic Services, Saskatoon, SK |
| CM-121 | $A^+$ $B^+$, Manitoba, Canada, (20 cases) 2000 |
| 29975 | A-B+ Manitoba, Canada (16 cases) 1998 |
| 05-2694 | $A^+$ $B^+$, Manitoba, Canada, (7 cases) 2005 |
| M13876 | Sherbrooke, QC, 2004 |
| M16256 | Sherbrooke, QC, 2004 |
| M23257 | Sherbrooke, QC, 2004 |
| M26195 | Sherbrooke, QC, 2004 |
| M46846 | Sherbrooke, QC, 2004 |
| M6510 | Sherbrooke, QC, 2005 |
| M7465 | Sherbrooke, QC, 2005 |
| M9349 | Sherbrooke, QC, 2005 |
| M6317 | Sherbrooke, QC, 2005 |
| M13340 | Sherbrooke, QC, 2005 |
| R20291 | $A^+B^+$, NAP1/027, UK, 2005 |
| CD196 | $A^+B^+$, NAP1/027, France, 1985 |
| M68 | $A^+B^+$, 017, Ireland, 2006 |
| CF5 | $A^+B^+$, 017, Belgium, 1995 |
| CD20 | 023, UK, 2007 |
| BI-6 | $A^+B^+$, USA, 2003 |

TABLE 1-continued

*C. difficile* strains.

| *C. difficile* strain | Characteristics |
|---|---|
| BI-11 | $A^+B^+$, USA, 2001 |
| BI-14 | $A^+B^+$, USA, 2004 |
| 001-01 | UK, 2008 |
| 106-01 | UK, 2007 |
| M120 | $A^+B^+$, 078, 2007 |
| BI-9 | 001, NAP2 |
| Liv022 | UK, 2009 |
| Liv024 | UK, 2009 |
| TL174 | UK, 2009 |
| TL176 | UK, 2009 |
| TL178 | Ireland, 2009 |
| VPI10463 | ATCC 43255, O87 |

To analyse LTA by HR-MAS (Example 2) a single agar plate was streaked for confluent growth and incubated for 12 h. Cells were scraped from BHI plate and killed for 4 h with 2% phenol prior to analysis. Cells were washed extensively (×4) in sterile PBS, followed by washes in PBS/$D_2O$. The washed cell pellets were re-suspended in 40 μL $D_2O$ containing 0.015% TPS (internal standard).

For broth-grown cells, 500 ml cultures were inoculated to a starting $OD_{600}$ of 0.1 using cells grown for 18 h on BHI agar plate. Flasks were incubated in anaerobic hood without shaking until $OD_{600}$ was 1.5-2.0 and then harvested by centrifugation.

Other Clostridia species (non *C. difficile*) that were examined are detailed in Table 2

TABLE 2

Other *Clostridia* species

| Clostridial species | Strain number |
|---|---|
| *C. botulinum* type I | A6 |
| *C. botulinum* type II | E Russ |
| *C. barati* | 4624 |
| *C. butyricum* | ATCC 19398 |
| *C. perfringens* | ATCC 13124 |
| *C. subterminale* | ATCC 25772 |
| *C. sporogenes* | ATCC 3584 |
| *C. bifermentans* | ATCC 638 |

Example 2: Whole Cell HR-MAS NMR

Whole, killed *C. difficile* isolate cells (from Example 1) were subjected to high resolution magic angle spinning (HR-MAS) NMR analysis to initially compare the surface polysaccharide profile of *C. difficile* isolates in a high-throughput manner. HR-MAS NMR provides a quick and rapid method to assess the surface glycoconjugates.

*C. difficile* cells from one plate of confluent growth of each isolate were killed in 2% phenol for 4 h prior to NMR analysis. HR-MAS NMR experiments were performed using a Varian Inova 500 MHz spectrometer equipped with a Varian nano-NMR probe as previously described (St. Michael et al, 2002, Young et al, 2002). Spectra from 40 μL samples were spun at 3 kHz and recorded at ambient temperature (21° C.) with the suppression of the HOD signal at 4.8 ppm. Proton spectra of bacterial cells were acquired with a Carr-Purcell-Meiboom-Gill (CPMG) pulse sequence (90-(τ-180-τ)$_n$-acquisition) to remove broad lines arising from lipids and solid-like material. The total duration of the CPMG pulse (n*2τ) was 1 ms with τ set to (1/MAS spin rate). The methyl resonance of 3-(trimethylsilyl)propionic-2,2,3,3-$d_4$ acid (TPS) (0.015% in $D_2O$) at 0.00 ppm was used as internal reference in $^1H$ spectra. The high resolution spectra of purified PS-II and O-deacylated LTA were used as references.

Figure 1A:
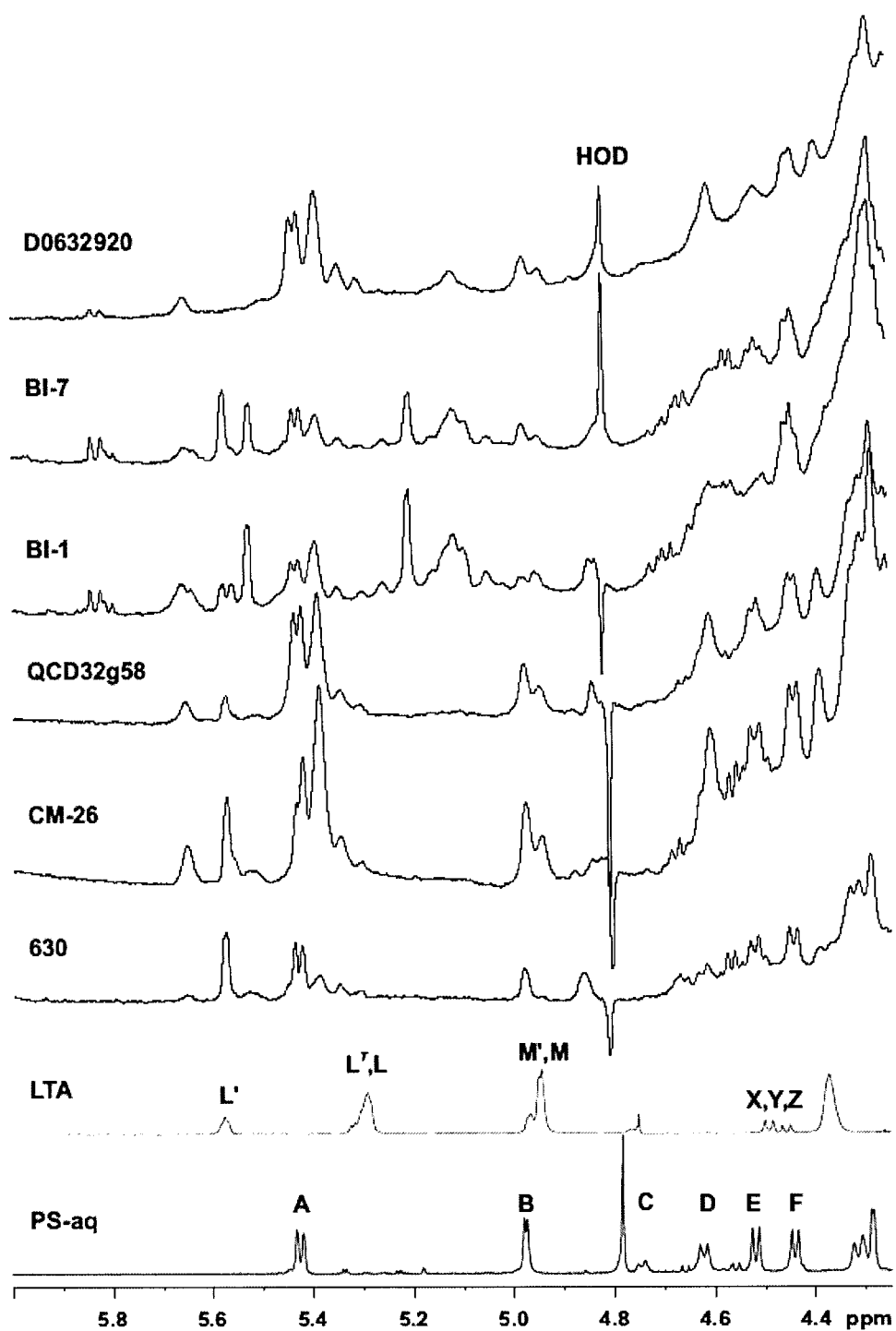
FIGS. 1A and 1B show results of whole cell HR-MAS NMR analysis of *C. difficile* isolates. For each isolate, the cells from one plate of confluent growth were killed in 2% phenol prior to analysis. As reference, the high resolution spectra of purified PS-II and O-deacylated LTA are shown on the bottom. The anomeric resonances are labelled according to the structures for the capsular polysaccharide and LTA in FIG. 3.
Figure 1B:
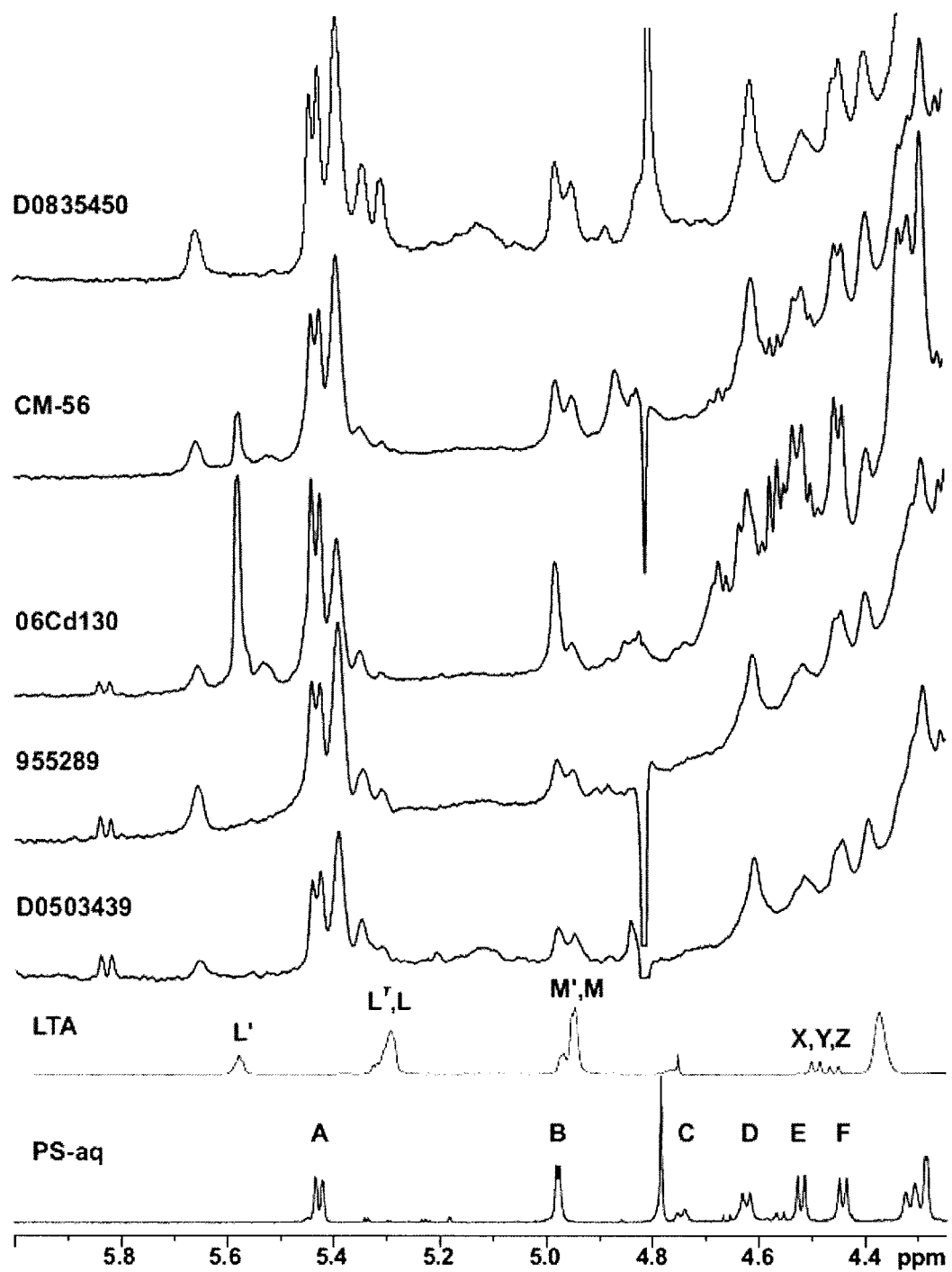

The anomeric region of the $^1H$ spectrum of strain 630 was compared to 10 different strains of either clinical or environmental sources (FIGS. 1A and B). The $^1H$ spectra indicated the presence of highly conserved capsular polysaccharide (PSII) and a conserved and structurally novel lipotechoic acid (LTA) in all the strains examined. Several anomeric resonances were observed and these correlated to the published chemical shifts for the anomeric resonances (FIG. 1) of the polysaccharide composed of a hexaglycosyl phosphate repeat unit reported by Ganeshapillai supra. In addition to anomeric signals correlating to the capsular polysaccharide structure, a number of additional conserved resonances were observed for each strain.

Example 3: Isolation and Purification of Surface Polysaccharides

In order to initially confirm the presence of the hexaglycosyl phosphate polysaccharide and to investigate the structure corresponding to the additional signals in HR-MAS NMR experiments (Example 2), and subsequently to prepare the structurally characterised LTA for glycoconjugation, three strains (630, VPI10463 and CM-26) were chosen for large scale growth, polysaccharide extraction, characterization of the isolated polysaccharides and provision of LTA for glycoconjugation.

In order to ensure that the polysaccharides extracted were from vegetative cells, cultures of strains 630, VPI10463, and CM-26 (Example 1) were harvested at late logarithmic phase ($OD_{600}$ 1.5-2.0). The bacterial cells were harvested (8200×g, 4° C., 20 min), killed with the addition of phenol to 4% washed with 10 mM phosphate buffered saline, pH 7.4, and subjected to modified hot water-phenol extraction. Briefly, the cells were first extracted in boiling water for 30 min and the resulting solution separated by low-speed centrifugation; the supernatant was dialyzed against tap water and lyophilized. Contaminating proteins and nucleic acids were removed by precipitation with trichloroacetic acid, followed by dialysis against water. The water-soluble material was separated by anion exchange chromatography on a HiTrap Q column using a $H_2O$-1M NaCl gradient to give a polysaccharide fraction (PS-II).

The remaining cells were subjected to extraction with 45% phenol (68° C., 30 min). The water phase was separated from the phenol phase and cell debris by centrifugation. The phenol phase and cell debris was then re-extracted with more water and treated as per above. The two water phases were combined and dialyzed against tap water until phenol-free, then lyophilized. The dried sample was dissolved in water to give a 1-2% solution (w/v) and treated with deoxyribonuclease I (DNase) (0.01 mg/ml) and ribonuclease (RNase) (0.01 mg/ml) for 3 hrs at 37° C., then treated with proteinase K (0.01 mg/ml) for 3 hrs. The sample was then dialysed against tap water for 17 hrs and lyophilized. The resulting crude polysaccharide sample was purified by anion exchange chromatography as described above. The LTA fraction was O-deacylated with 14% ammonia in 10% methanol (50° C., 3 h), yielding a deacylated polysaccharide. The solution was rotary evaporated to dryness, re-dissolved in water, and gel-purified on a Sephadex G-25 column (Amersham), eluting with water.

The following three methodologies were utilised for structural analyses.

Liberated fatty acids were analyzed as fatty acid methyl esters (FAMEs) as previously described (Ichihara & Fukubayashi, 2010 J. Lipid Res, 51: 635-40).

When required, samples were re-N-acetylated by treatment with acetic anhydride and subsequent column chromatography. Similarly, if required re-N-acetylated samples were de-O-acetylated by treatment with mild base and purified by subsequent column chromatography as required.

Carbohydrate samples were dephosphorylated by treatment with 48% HF (Sigma Aldridge, Oakville, ON) for 48 hrs at 4° C. The HF was evaporated under stream of nitrogen and the residue re-dissolved in water and lyophilized.

Example 4: Structural Analysis of the LTA

The polysaccharide fractions (PS-II, LTA) obtained in Example 3 were subject to gas chromatography, nuclear magnetic resonance (NMR) and mass spectroscopy experiments in order to identify monosaccharides and determine the polysaccharide structure.

Monosaccharides were identified by GC on a Shimadzu GC-14 gas chromatograph equipped with flame ionization detector and Zebron ZB-5 capillary column (30 m×0.25 mm), with hydrogen as carrier gas, using a temperature gradient 170° C. (3 min), 260° C. at 5° C. $min^{-1}$. Prior to analysis, polysaccharides were hydrolyzed with 4 M TFA (110° C., 3 h) and converted to alditol acetates by conventional methods. Methylation analysis was performed. Methylated glycerophosphorylated glucans were dephosphorylated prior to alditol acetate derivatization. Partially methylated alditol acetates were analyzed by GC and GC-MS. GC-MS experiments were performed on a Varian Saturn 2000 system, equipped with DB-17 (30 m×0.25 mm) fused-silica column using a temperature gradient of 180° C. (2 min) to 240° C. at 2° C. $min^{-1}$; equipped with a ion-trap mass spectral detector. Polysaccharides and standards of L-glyceric acid with R- and S-2-butanol were mixed with acetyl chloride (0.3 mL of 2-BuOH, 0.03 mL of AcCl) and heated for 3 h at 90° C., dried under air stream, acetylated with Ac2O-Py (1 h, 90° C.), dried and analyzed by GC-MS on Varian Saturn 2000 MSD on DB17 column at 140° C. isothermally.

NMR spectra were acquired using a Varian INOVA 500 MHz spectrometer employing standard software at 25-45° C. using a 5 mm indirect detection probe with the $^1H$ coil nearest to the sample (Brisson et al, 2002). Samples were dissolved in $D_2O$ using acetone as internal reference (2.23 ppm for $^1H$ and 31.5 ppm for $^{13}C$). Polysaccharide samples were analyzed using standard pulse sequences DQCOSY, TOCSY (mixing time 120 ms), NOESY (mixing time 400 ms), HSQC and HMBC (100 ms long range transfer delay). $^1H$-$^{31}P$ HMQC and HMQC-TOCSY were run with $^1H$-$^{31}P$ coupling set to 11 Hz, TOCSY mixing time 100 ms. Molecular models were generated using the InsightII software.

Structural analysis of the capsular polysaccharide (PS-II) using NMR (DQCOSY, TOCSY, NOESY, $^1H$-$^{13}C$ HSQC, $^1H$-$^{13}C$ HMBC, $^1H$-$^{31}P$ HMQC, $^1H$-$^{31}P$ HMQC-TOCSY), data not shown, led to the complete assignment of all signals and the structure presented (FIGS. 2A and 3) on the basis of signal position, coupling constants, NOE and HMBC correlations. However, due to the overlap of signals of H-2 and H-3 of residue A, it was not possible to determine its identity. This monosaccharide was linked to a phosphate, which followed from $^1H$-$^{31}P$ correlation spectrum. Dephosphorylation of the PS-II with 45% HF gave a pentasaccharide (OS-aq), representing the repeating unit of this polysaccharide. Residue A was present at the reducing end of the OS-aq in α- and β-configurations, where vicinal coupling constants corresponded to manno-configuration (data not shown). NMR data were in close agreement with that published by Ganeshapillai et al (2008) confirming that the structure of PS-II isolated from 630 and CM26 was identical to that previously reported for three other strains of *C. difficile*, (Ganeshapillai et al, 2008). No evidence for a distinct rhamnose-containing polysaccharide (PS-I), identified in the study by Ganeshapillai et al 2008, was observed for *C. difficile* strains 630 and CM26 examined presently.

The proton NMR spectrum of the phenol-extracted LTA showed strong signals of fatty acids at 0.83 and 1.35 ppm. Fatty acid analysis of this mixture showed the presence of C14:0 (minor), C16:0, C16:1, C18:0 and C18:1 acids. After O-deacylation to remove fatty acids, major anomeric signals (L, M) and minor signals (L', M', $L^T$, X, Y, Z) were observed in the $^1H-^{13}C$ HSQC correlation spectrum (FIG. 2B-1), which permitted complete NMR structural analysis using the same methods as outlined above. The novel LTA contained a repeating unit comprising two GlcpNAc residues (L-M) connected by an α(1-3) linkage and D-glyceric acid (GroA) as an aglycon. The repeating units were connected by a 6-6 phosphodiester bridge (6-P-6) between C-6 of residue L and C-6 of residue M. This portion of the structure was previously found in cell-envelope polysaccharide antigens of the Gram positive organism, *Peptostreptococcus anaeorobius* (Storz et al, 1990). The terminal unit $L^T$, which is the non-reducing GlcpNAc(1-3) residue, with no phosphate at C-6 was also detected.

Figure 2B:
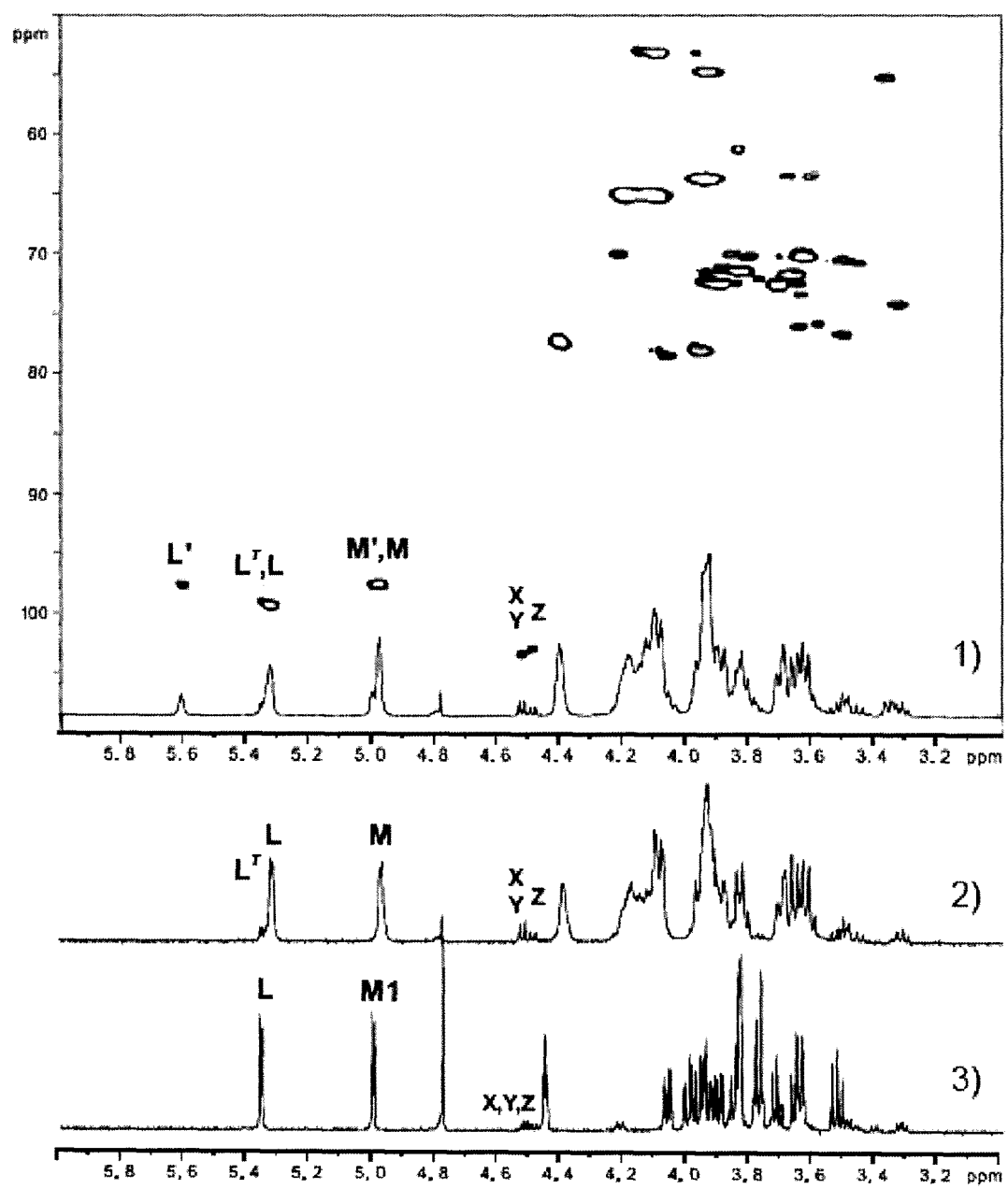
FIG. 2B shows the NMR spectra of lipoteichoic acid (LTA) from *C. difficile* CM-26. 1). The proton spectrum and $^1$H-$^{13}$C HSQC correlation spectrum of the O-deacylated LTA with the anomeric resonances labelled for the L-M and L'-M' repeating units, the terminal unit $L^T$, and the core unit X-Y-Z. 2). The proton spectrum of the N-acetylated O-deacylated polymer showing the disappearance of L' and M' resonances due to N-acetylation of the GlcpN(1→3) residue (L'). 3). The proton spectrum of the dephosphorylated N-acetylated oligosaccharides OS-1 and OS-II from the repeating units (L-M) and from the core unit (X-Y-Z).

A minor component, GlcpN, labelled L' was observed due to substitution of the N-acetyl group at C-2 for N. De-acetylation at C2 resulted in the high field shift of H-2 at 3.37 ppm (L') compared to 3.94 ppm for H-2 (L). Different chemical shifts were also observed for the anomeric and H-3 resonances of residues L and L'. The presence of GlcpN also affected the resonances of the other GlcpNAc residue in the repeat unit, labelled M'(Table 2). Based on integration of the proton anomeric resonances, it was determined that ~30% of residues at position L in the LTA polymer were GlcpN. This was confirmed by N-acetylation, which led to disappearance of resonances for units L' and M' (FIG. 2B-2). Dephosphorylation of LTA produced the disaccharide OS-I (FIGS. 2B-3, and 3) consistent with a 6-6 phosphodiester bridge joining the repeating units.

TABLE 3

NMR data for O-deacylated LTA. Proton and $^{13}C$ chemical shifts (ppm).

| Unit | Atom | 1 | 2 | 3 | 4 | 5 | 6 (a/b) |
|---|---|---|---|---|---|---|---|
| GlcpNAc(1-3) L | H | 5.33 | 3.94 | 3.66 | 3.63 | 3.71 | 4.09/4.20 |
|  | C | 99.3 | 54.7 | 71.7 | 70.1 | 72.5 | 65.2 |
| GlcpN(1-3) L' | H | 5.62 | 3.37 | 3.80 | 3.63 | 3.71 | 4.09/4.20 |
|  | C | 97.7 | 55.2 | 70.1 | 70.1 | 72.5 | 65.2 |
| GlcpNAc(1-3) $L^T$ | H | 5.35 | 3.91 | 3.66 | 3.63 | 3.71 | 3.84/3.84 |
|  | C | 99.0 | 54.7 | 71.7 | 70.1 | 72.5 | 61.2 |
| GlcpNAc(1-2) M | H | 4.98 | 4.10 | 3.95 | 3.83 | 3.90 | 4.12/4.17 |
|  | C | 97.6 | 53.1 | 78.0 | 71.3 | 72.5 | 64.9 |
| GlcpNAc(1-2) M' | H | 5.00 | 4.15 | 4.06 | 3.88 | 3.90 | 4.12/4.17 |
|  | C | 97.6 | 52.9 | 78.4 | 71.2 | 72.5 | 64.9 |
| Glyceric acid N | H |  | 4.41 | 3.92/3.96 |  |  |  |
|  | C | 175.1 | 77.2 | 63.7 |  |  |  |
| Glcp(1-6) X | H | 4.52 | 3.34 | 3.50 | 3.44 | 3.58 | 4.08/4.19 |
|  | C | 104.1 | 74.2 | 76.6 | 70.5 | 75.7 | 65.0 |
| Glcp(1-6) Y | H | 4.52 | 3.32 | 3.50 | 3.50 | 3.64 | 3.86/4.21 |
|  | C | 104.1 | 74.2 | 76.6 | 70.4 | 76.0 | 69.9 |
| Glcp(1-1) Z | H | 4.49 | 3.32 | 3.50 | 3.46 | 3.64 | 3.86/4.21 |
|  | C | 103.7 | 74.2 | 76.6 | 70.6 | 76.0 | 69.9 |
| Glycerol | H | 3.77/3.92 |  | 3.61/3.68 |  |  |  |
|  | C | 72.0 |  | 63.4 |  |  |  |

The structure of the component X-Y-Z and glycerol could also be deduced from the NMR data (Table 3). All resonances could be assigned with the exception of H/C-2 signals of glycerol, which were not identified due to low intensity and signal overlap. Residues XY-Z and glycerol were found to correspond to the structure –P-6)-β-Glcp-(1-6)-β-Glcp-(1-6)-β-Glcp-(1-1)-Gro. Glycerol was originally esterified with fatty acids and removed after O-deacylation. The terminal glucose is phosphorylated and is substituted by GlcpNAc of the repeating unit (L-M) through a 6-6 phosphodiester bridge. The oligosaccharide OS-II derived from dephosphorylation of LTA (FIGS. 2B-3) is also consistent with the structures shown in FIG. 3. Integration of the major anomeric resonances for L, M and the minor ones for $L^T$, X, Y, and Z (FIG. 2B-2) indicated repeating units with a degree of polymerization less than 10. Analysis of HR-MAS spectra of strain CM-26 and comparison with the $^1H$ spectrum of purified deacylated LTA allowed for the assignment of the LTA signals observed in FIG. 1.

The sequence of sugars within the LTA was confirmed by mass spectrometry. A Prince CE system (Prince Technologies, The Netherlands) was coupled to a 4000 Q-Trap mass spectrometer (Applied Biosystems/MDS Sciex, Canada). A sheath solution (isopropanol-methanol, 2:1) was delivered at a flow rate of 1.0 uL/min. Separations were obtained on about 90 cm length bare fused-silica capillary using 15 mM ammonium acetate in deionized water, pH 9.0. The 5 kV of electrospray ionization voltage was used for positive ion mode. Tandem mass spectra were obtained using enhance production ion scan mode (EPI) with a scan rate of 4000 Da/s, in which the precursor ions were generated with an orifice voltage of +380 V.

Figure 4:
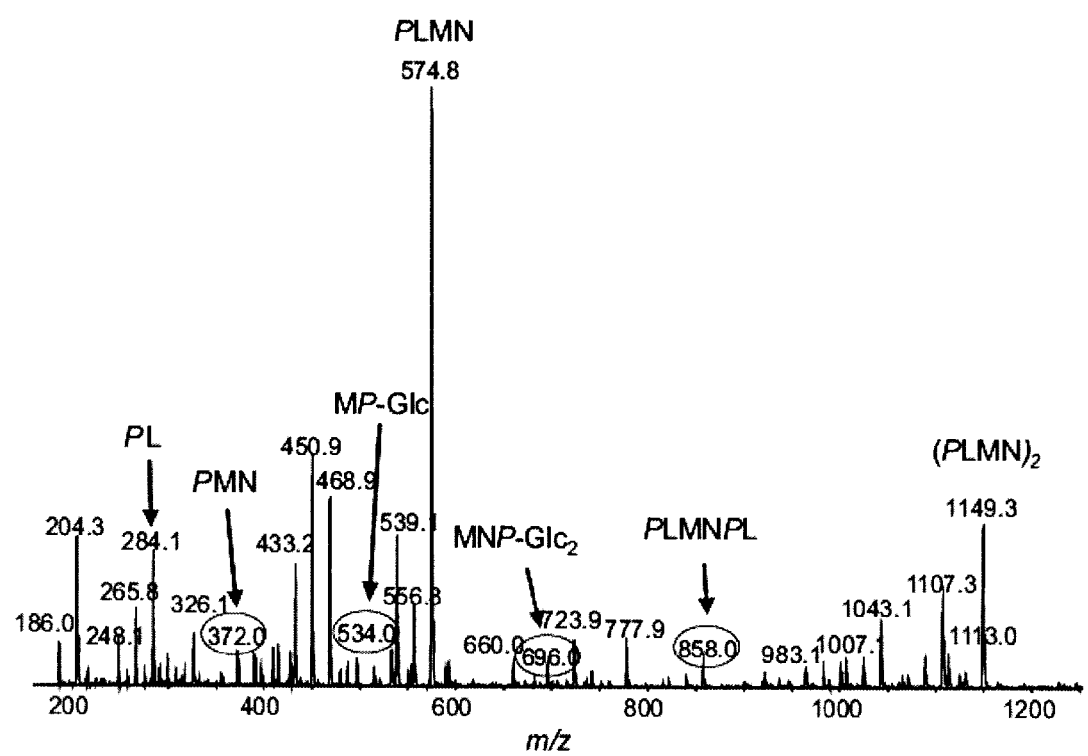
FIG. 4 shows an extracted mass spectrum of the LTA from *C. difficile*. Separation conditions: bare fused-silica (90 cm×50 μm i.d., 375 μm o.d.), 15 mM ammonium acetate, pH 7.0, +20 kV, 300 mbar. Ionization voltage: +5200 V. Orifice voltage: +350 V.

Because of its large molecular mass, a high orifice voltage (+350 V) was used to promote in-source collision-induced dissociation to facilitate its analysis with CE-MS (FIG. 4). The results were in complete agreement with the proposed structure (Table 4). The most abundant ion at m/z 574.8 corresponds to a single repeating unit (P, L, M, N). The ions correlated to a double repeating unit were detected at m/z 1149.3.

TABLE 4

CE-MS data and corresponding fragment compositions of the LTA from *C. difficile*. Monoisotopic mass units were used for calculation of m/z based on proposed composition as follows: Glc, 162.05; GlcNAc, 203.08; Gro, 88.08; P (phosphate), 79.97. $L^T$, L and M represent GlcNAc. L' is for GlcN and N is for glyceric acid (GroA).

| Ion ([M + H]$^+$) | | |
|---|---|---|
| Observed | Calculated | Fragment composition |
| 204.3 | 204.1 | GlcNAc |
| 284.1 | 284.1 | P + GlcNAc |
| 372.0 | 372.1 | P + GlcNAc + GroA (PMN) |
| 433.2 | 433.1 | P + 2GlcNAc—3H$_2$O (PLM) |
| 450.9 | 451.1 | P + 2GlcNAc—2H$_2$O (PLM) |
| 468.9 | 469.1 | P + 2GlcNAc—H$_2$O (PLM) |
| 534.0 | 534.2 | P + GlcNAc + GroA + Glc (MNP-Glc) |
| 539.1 | 539.4 | P + 2GlcNAc + GroA-2H$_2$O (PLMN) |
| 556.8 | 557.4 | P + 2GlcNAc + GroA-H$_2$O (PLMN) |
| 574.8 | 575.4 | P + 2GlcNAc + GroA (PLMN) |
| 696.0 | 696.3 | P + GlcNAc + GroA + 2Glc (MNP-Glc-Glc) |
| 723.9 | 724.3 | P + 3GlcNAc + GroA-3H$_2$O (L$^T$MNPL) |
| 777.9 | 778.3 | P + 3GlcNAc + GroA (L$^T$MNPL) |
| 858.0 | 858.2 | 2P + 3GlcNAc + GroA (PLMNPL) |
| 1007.1 | 1007.3 | 2P + 4GlcNAc + GroA-3H$_2$O (LMPLMN) |
| 1025.1 | 1025.3 | 2P + 4GlcNAc + GroA-3H$_2$O (LMPLMN) |
| 1043.1 | 1043.3 | 2P + 4GlcNAc + GroA-H$_2$O (LMPLMN) |
| 1107.3 | 1107.4 | 2P + 3GlcNAc + GlcN + 2GroA (LMPL'MN) |
| 1149.3 | 1149.4 | 2P + 4GlcNAc + 2GroA (PLMN)$_2$ |

The sequence of sugars within the LTA was also corroborated by mass spectrometry (performed as described above). The presence of ions at m/z 534.0 and 696.0 indicated two glucose residues attached to MNP. In combination with evidence from the NMR experiment, it was thus concluded that the fatty acids and the core is linked through the glucose residues.

Figure 5:
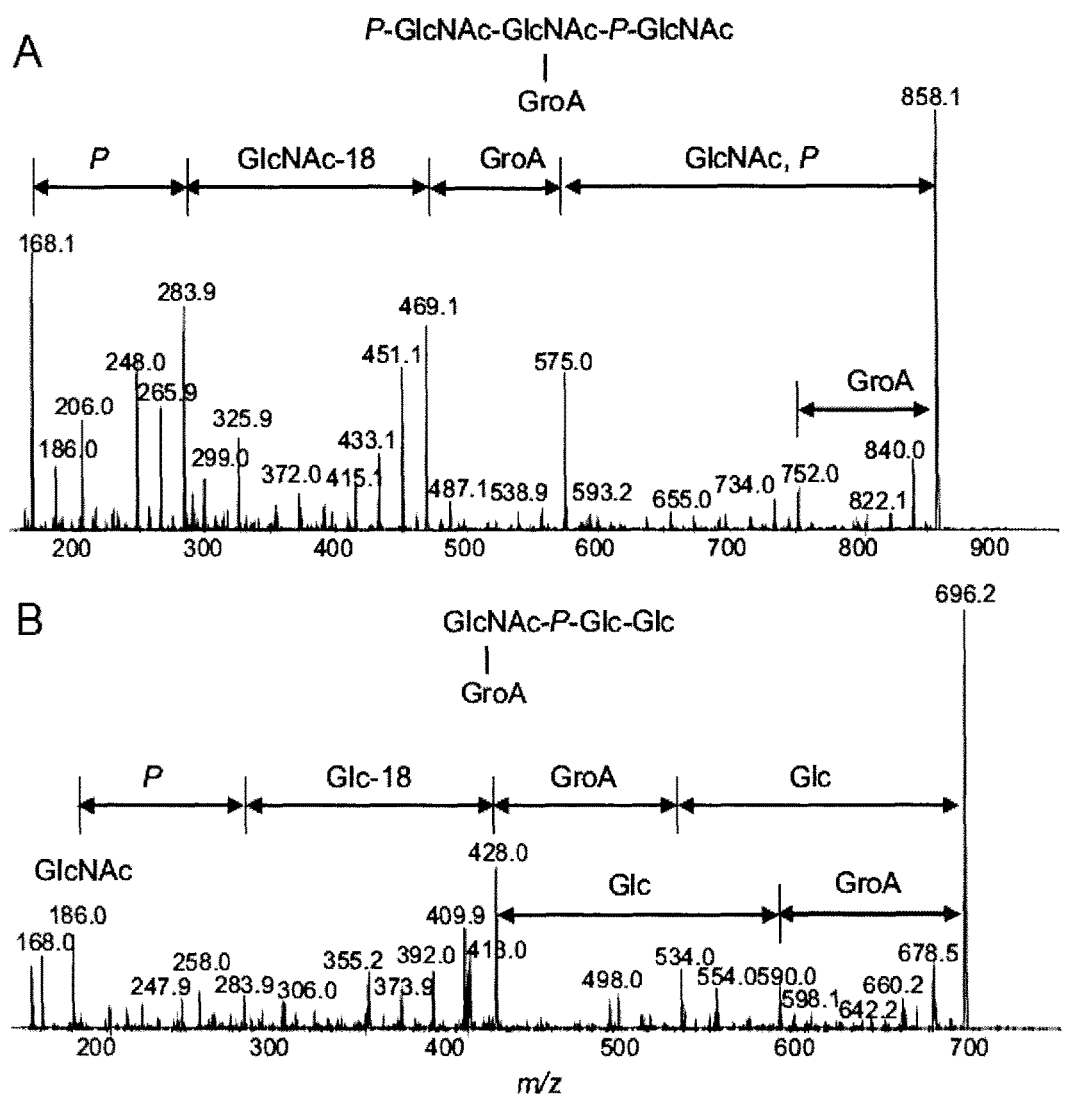
FIG. 5 shows CE-MS/MS analyses (positive ion mode, orifice voltage 350 V) of the LTA from *C. difficile*.
Figure 6:
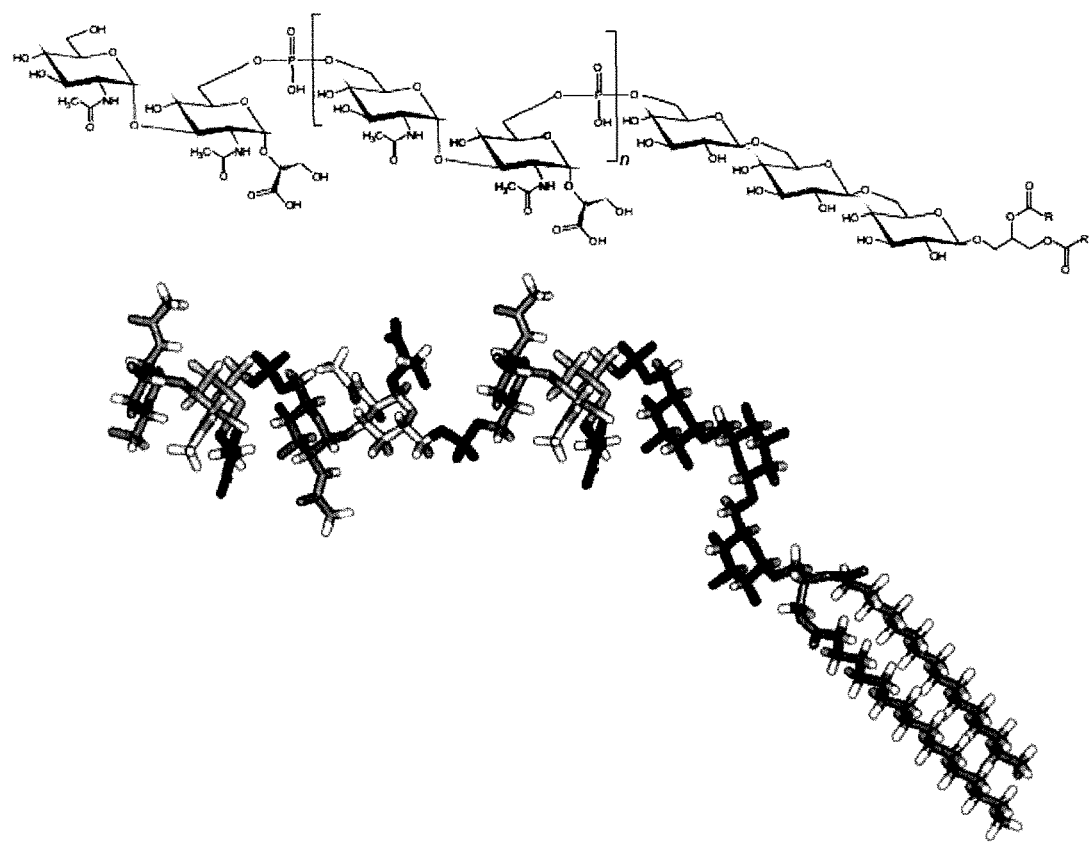
FIG. 6 shows the structure of the major lipoteichoic acid (LTA) from *C. difficile*. Glycerol (Gro) is esterified either to $C_{14}$, $C_{16}$, or $C_{18}$, saturated or mono-unsaturated fatty acids indicated by R. A molecular model of the LTA with three repeat units and a $C_{16}$ saturated fatty acid is shown.

The product-ion spectra obtained from the second generation ions at m/z 858.0 and 696.0 are presented in FIGS. 5A and 5B, respectively. The series of fragments correspond to the proposed structure for the LTA (FIG. 6). Observation of sequential loss of the residues Glc, N, Glc, P and GlcNAc (FIG. 5B) confirms again that two glucose residues are linked to the repeat unit. The assignments for other fragment ions are given in Table 4.

Example 5: Production of Polyclonal Antisera to Bacterial Cells

In order to determine if the purified LTA was recognised as an immunogen in the context of the intact bacterial cell, polyclonal antisera to formalin killed whole cells of *C. difficile* strains 630 and R20291 was produced. For strain 630, a New Zealand white rabbit (1.5-2 kg) was immunised with 2×0.25 ml subcutaneous injections containing 2×10$^9$ bacterial cells mixed 1:1 with incomplete Freunds adjuvant (IFA) and boosted three times (D28, 56 and D77) with an identical antigen preparation. For strain R20291 another New Zealand white rabbit (1.5-2 kg) rabbit was immunised with 2×0.25 ml subcutaneous injections containing 2×10$^9$ bacterial cells mixed 1:1 in incomplete Freunds adjuvant (IFA) and boosted two times (D28, D56) with the identical antigen preparation.

Figure 7:
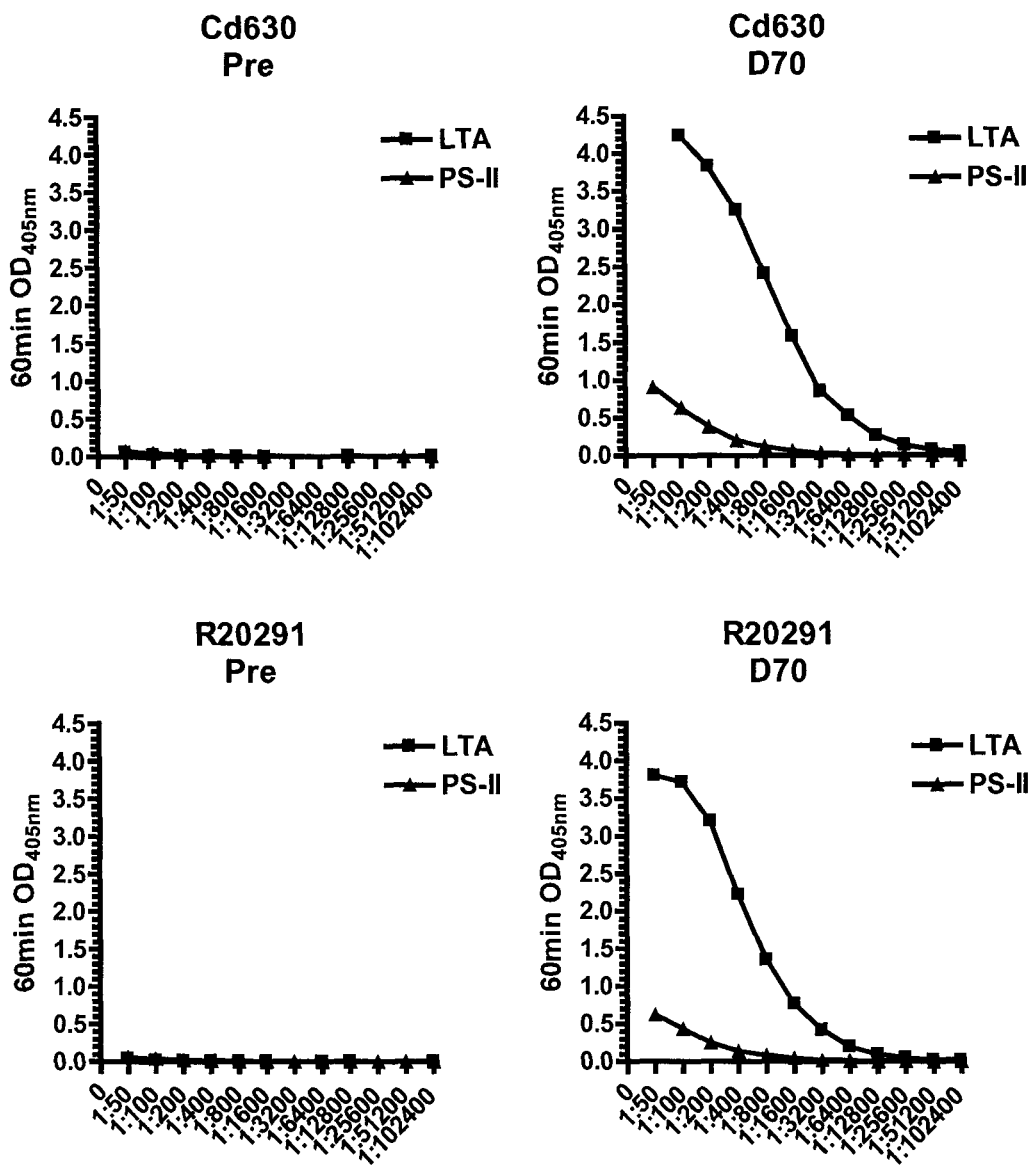
FIG. 7 shows the titration of the polyclonal sera derived from rabbit immunisations with killed whole cells from strains 630 and R20291 against purified LTA and PS-II antigens

FIG. 7 illustrates the ELISA determination of recognition of LTA and polysaccharide capsule (PS-II) with titration of post-immune rabbit sera following immunization with bacterial cells. ELISA values after 60 min at OD$_{405}$ nm are detailed on the y-axis and dilutions are shown on the x-axis. Plates were coated with 1 ug of LTA or 1 ug of PS-II per well.

The polyclonal antisera raised to *C. difficile* 630 and R20291 cells revealed a good titer towards LTA (630 sera diluted 1:800 gave an OD of 2.5; R20291 sera diluted 1:800 gave an OD of 1.4) and a lower titer towards PS-II (630 (1:100) OD=0.7; R20291 (1:100) OD=0.4)

The polyclonal sera raised to the Cd 630 strain whole cells was then tested for its ability to recognise a variety of other *C. difficile* strains and other Clostridial species (Table 5).

TABLE 5

ELISA determination of recognition of whole cells of *C. difficile* strains and other Clostridial species (as indicated) with post-immune CD630 rabbit polyclonal sera (D105). ELISA values after 60 min. at OD$_{405\ nm}$ are detailed. Dilutions are shown in parentheses.

| *C. difficile* Strain | Whole cell Rabbit Sera (1:200) CD1 |
|---|---|
| Cd630 | 3.104 |
| QCD | 1.161 |
| R20291 | 1.123 |
| M120 | 0.886 |
| CM26 | 1.362 |
| 106-01 | 2.005 |
| Cd196 | 2.869 |
| 001-01 | 3.007 |
| Cd20 | 2.854 |
| B1-14 | 1.986 |
| B1-11 | 2.146 |
| B1-9 | 1.710 |
| B1-6 | 1.883 |
| CM121 | 1.331 |
| CM56 | 1.798 |
| O6CD130 | 1.851 |
| 29975 | 1.997 |
| M13876 | 1.573 |
| M16256 | 1.579 |
| B1-1 | 1.621 |
| 052694 | 1.822 |
| B1-7 | 1.616 |
| M26195 | 1.999 |
| M23257 | 1.296 |
| M46846 | 1.483 |
| LIV022 | 1.135 |
| TL178 | 1.184 |
| LIV024 | 1.252 |
| TL176 | 1.173 |
| CD305 | 0.909 |
| CF5 | 1.332 |
| M6510 | 1.249 |
| TL174 | 1.290 |
| M68 | 0.910 |
| M6317 | 1.056 |
| M7465 | 1.108 |
| M9349 | 1.001 |
| M13340 | 1.135 |
| VPI 10463 | 1.618 |
| D0724491 | 0.879 |
| D0835450 | 1.202 |
| 955289 | 1.070 |
| *C. perfringens* | 0.286 |
| *C. sporogenes* | 0.241 |
| *C. barati* | 0.853 |
| *C. butyricum* | 1.361 |
| *C. subterminale* | 1.629 |
| *C. bifermentans* | 1.723 |
| *C. botulinum* type I A6 | 0.416 |
| *C. botulinum* type II E Russ | 0.129 |

Example 6: Preparation of Conjugates from Purified LTA (i) Human Serum Albumin (HSA) and Maleimide (BMPH) Linker The glycoconjugate to assess the immunogenic potential of the LTA was prepared as described below.

Figure 8:
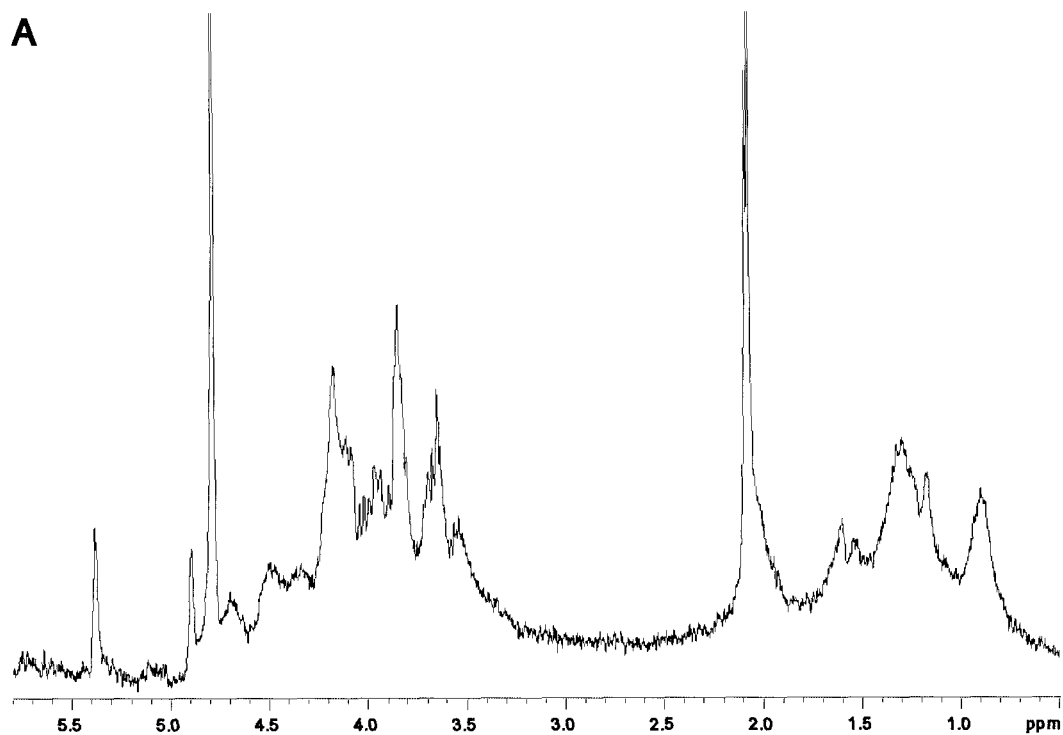
FIG. 8 shows the NMR spectra of the LTA from *C. difficile* strain 630 before (FIG. 8A) and after (FIG. 8B) O-deacylation and after both O-deacylation and linker incorporation (FIG. 8C).
Figure 8:
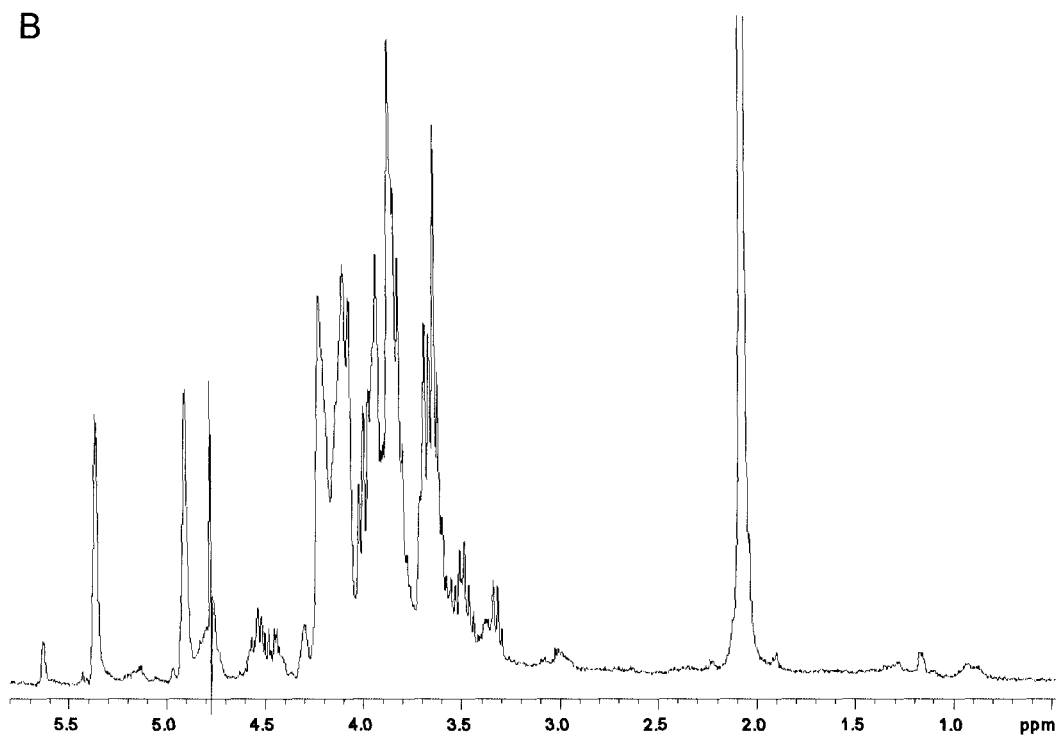
Figure 8:
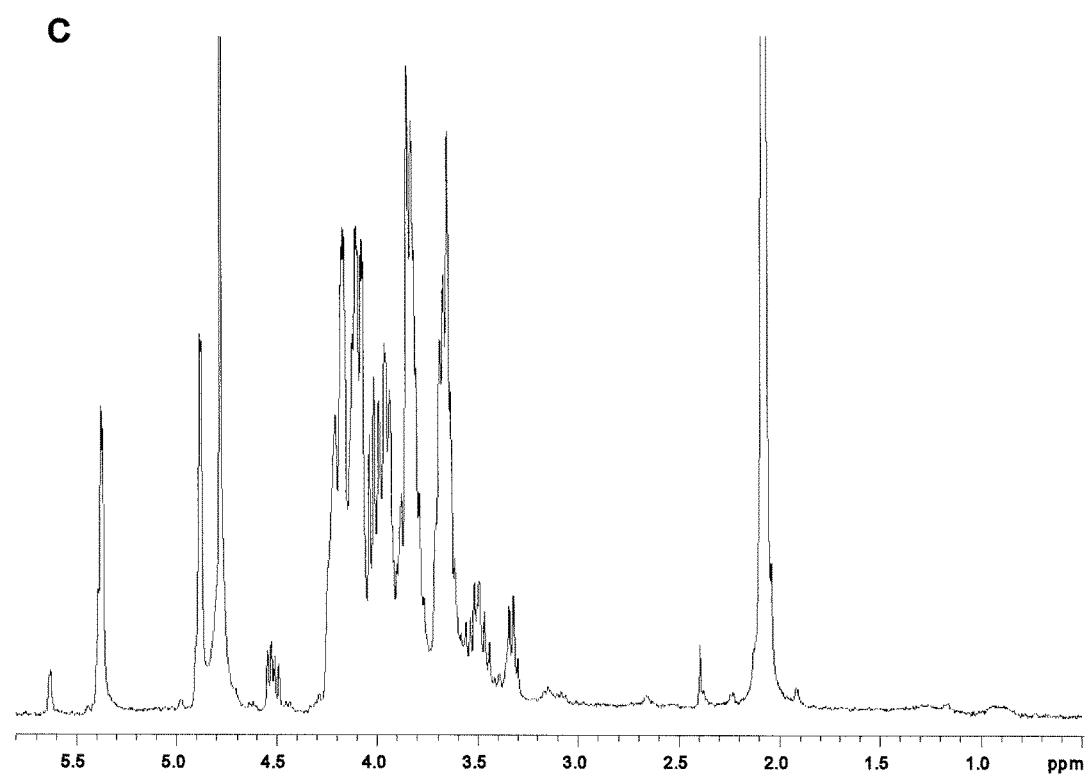

O-deacylation: Purified LTA (Example 3) was treated with 14% $NH_4OH$ in 10% MeOH at 50° C. for 3 h. The solution was rotary evaporated to dryness, re-dissolved in water, and gel-purified on a Sephadex G-25 column (Amersham), eluting with water. The product fraction was collected and lyophilised to prepare O-deacylated LTA (LTA-OH). The extent and specificity of O-deacylation was monitored by NMR (as described in Example 4), as evidenced by the loss of the signals for the $CH_2$ residues at 0.5 to 1.5 ppm (FIGS. 8A and B).

Attachment of linker molecule: LTA-OH (4 mg/ml) was dissolved in 200 mM sodium phosphate at pH 7.5 and a 3× molar equivalent of N-succinimidyl-5-acetylthiopropionate (SATP, Pierce) dissolved in 100 µl of DMSO (BDH Chemicals) was added. The reaction was left at 22° C. for 2 h in the dark. The sample was then purified using a Sephadex G-25 column, eluting with water and the product peak was lyophilised. The product was monitored by NMR as described in Example 4. NMR revealed the acquisition of a singlet at 2.4 ppm corresponding to the methyl protons of the acetate protecting group consistent with attachment of the linker molecule and the concomitant decrease in the anomeric resonance of the free amino sugar targeted by the linker (FIG. 8C).

Activation of protein carrier: In order to conjugate the protein carrier molecule HSA to the thiol-tagged LTA, it was necessary to modify the carboxyl groups on the HSA protein (15 mg) by treatment with an 600× molar excess of 1-ethyl-3-(3-dimethylaminopropyl) carbodiimide hydrochloride (EDC, Pierce) and a 80× molar excess of N-(β-maleimido-propionic acid) hydrazide trifluoroacetic acid salt (BMPH, Pierce) dissolved in 3 ml of 100 mM 2-(N-morpholino) ethanesulfonic acid (MES, Aldrich) at pH 5.2 at 4° C. for 16 h. The sample was purified on a Sephadex G-25 column, eluting with 100 mM sodium phosphate pH 6.8. The product peak was concentrated to approximately 0.5 ml using an Amicon ultra-15 10 kDa MMCF spin column and stored at 4° C.

Figure 9:
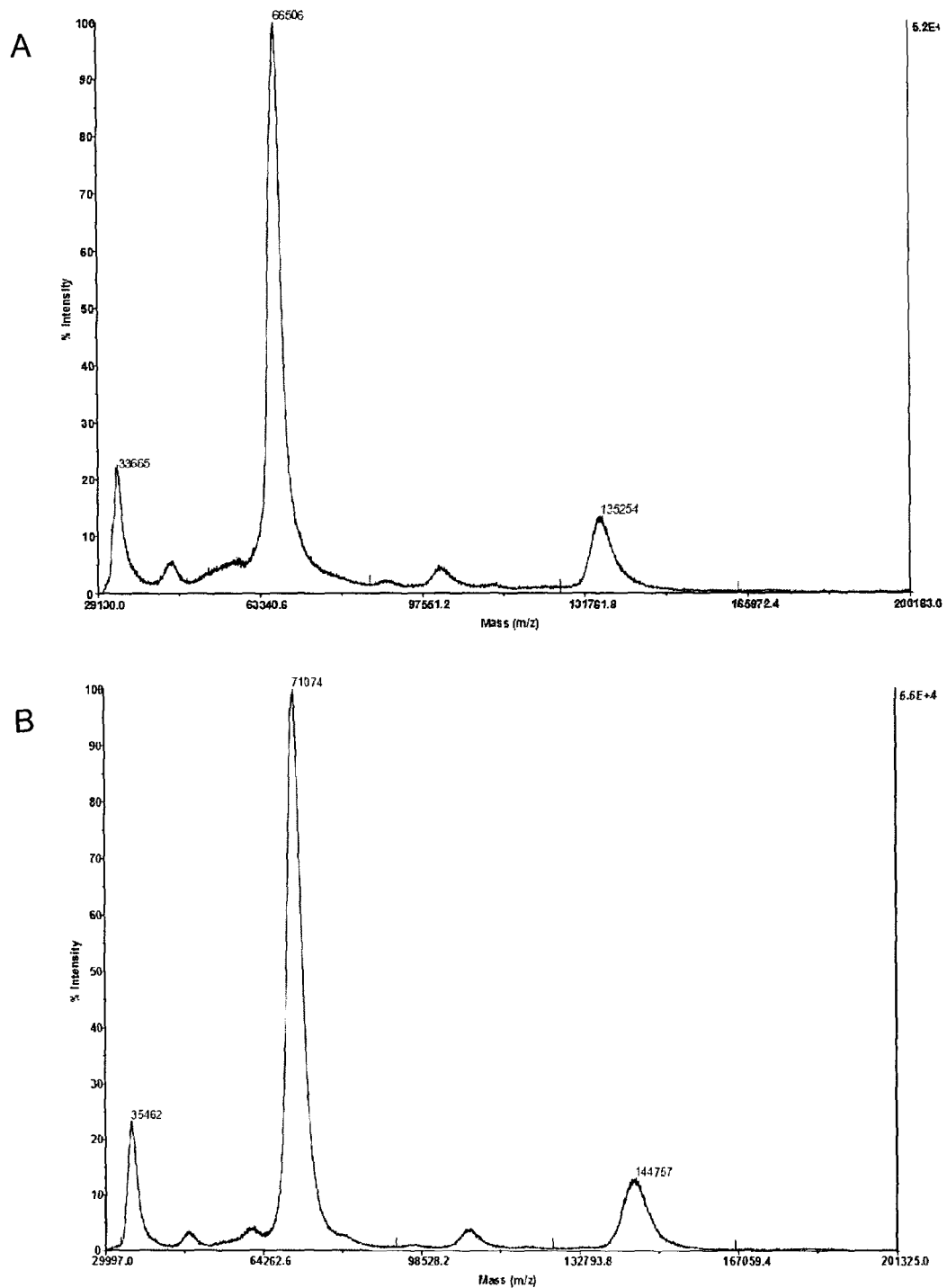
FIG. 9 shows MALDI-TOF mass spectroscopy analyses of HSA (FIG. 9A), HSA-BMPH (FIG. 9B), and HSA-BMPH-SH-LTA conjugate (FIG. 9C).
Figure 9:
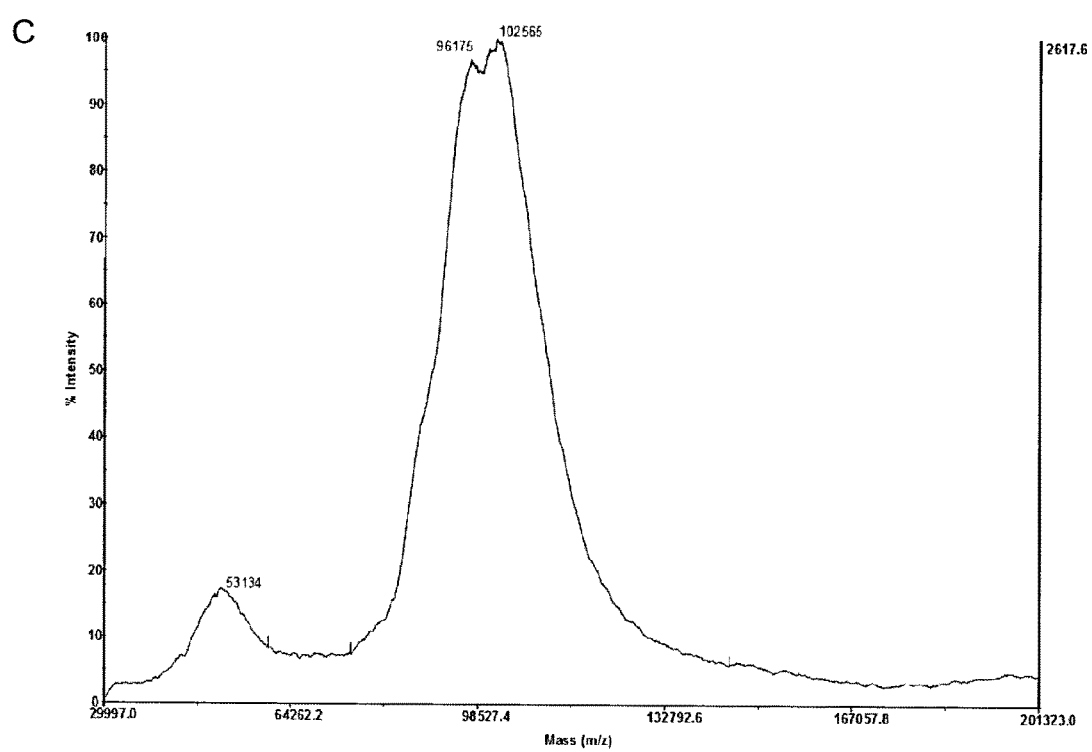

The activated protein was characterised by MALDI-TOF MS. Briefly, matrix-assisted laser desorption ionization-time of flight (MALDI-TOF) mass spectra were obtained using a Voyager DE-STR mass spectrometer (Applied BioSystems, Foster City, Calif., U.S.A.). The instrument was operated in positive, linear ion mode under delayed extraction conditions (200 ns) using an accelerating voltage of 25 000 V. Each spectrum is the average of approximately 100 laser shots. The matrix used was 3,5-dimethoxy-4hydroxy cinnamic acid (sinapinic acid), prepared at a concentration of 10 µg/µl in 30% acetonitrile and 0.1% formic acid (v/v). These solutions were spotted directly on the MALDI target in a 1:3 ratio with matrix. MALDI-TOF of activated HSA showed that ~25 carboxyl residues had been activated with BMPH as evidenced by a mass increase of ~4.6 kDa (FIG. 9B) over inactivated HSA (FIG. 9A).

Conjugation reaction: The thiol protecting group of the carbohydrate (5 mg/ml) was removed using 100 mM hydroxylamine hydrochloride (JT Baker) in 100 mM sodium phosphate pH 6.8 at 22-24° C. for 1.5 h under nitrogen. The sample was purified on a Sephadex G-25 column, eluting with 100 mM sodium phosphate pH 6.8. The eluted product was collected directly into the maleimide-activated protein. The mixture was left to react at 22-24° C. for 3 h in the dark under nitrogen while rocking. This mixture was then left for 16 h at 4° C. and concentrated to ~1 ml as described above. The concentrate was washed and concentrated a further four times using Dulbecco's PBS (Gibco) containing 10 mM sodium citrate (Sigma). The final concentrate was stored at 4° C. The glycoconjugate was characterised by MALDI-TOF MS as described above. Results (FIG. 9C) suggested that ~5 carbohydrate molecules had been attached per carrier protein, and revealed a mass increase of ~31.5 kDa overall that corresponds to 5 units of ~6.5 kDa for each carbohydrate unit attached. This indicated that the LTA polymer attached to HSA was approximately 15 repeat units in length.

(ii) Human Serum Albumin (HSA) and Bromoacetyl (BrAc) Linker

A glycoconjugate to assess the immunogenic potential of the LTA was prepared wherein the carrier protein was human serum albumin (HSA) and the linker on the protein was based on bromoacetyl (BrAc). The LTA was activated as is or following O-deacylation and the linker was based on thiol (SATP).

O-deacylation and linker attachment: The purified LTA was O-deacylated as described above. Purified LTA and O-deacylated LTA had a SATP linker attached as described above.

Activation of protein carrier: In order to conjugate the protein carrier molecule HSA to the thiol-tagged LTA or LTA-OH, it was necessary to modify the amino groups on the HSA protein (15 mg) by dissolving it in 4 ml of 100 mM sodium phosphate at pH 8 and adding a 200× molar excess of bromoacetic acid N-hydroxysuccinimide ester (Sigma) in 200 µl of DMSO (BDH Chemicals). The reaction was left for 17 hrs at 4° C. then purified, concentrating the sample 4× with 10 ml of 100 mM sodium phosphate at pH6.8 in an Amicon ultra-15 30 kDa MMCF spin column and stored at 4° C.

The activated protein was characterised by MALDI-TOF MS as described above. MALDI-TOF of activated HSA showed that ~38 amino residues had been activated with bromoacetic acid N-hydroxysuccinimide ester.

Figure 10:
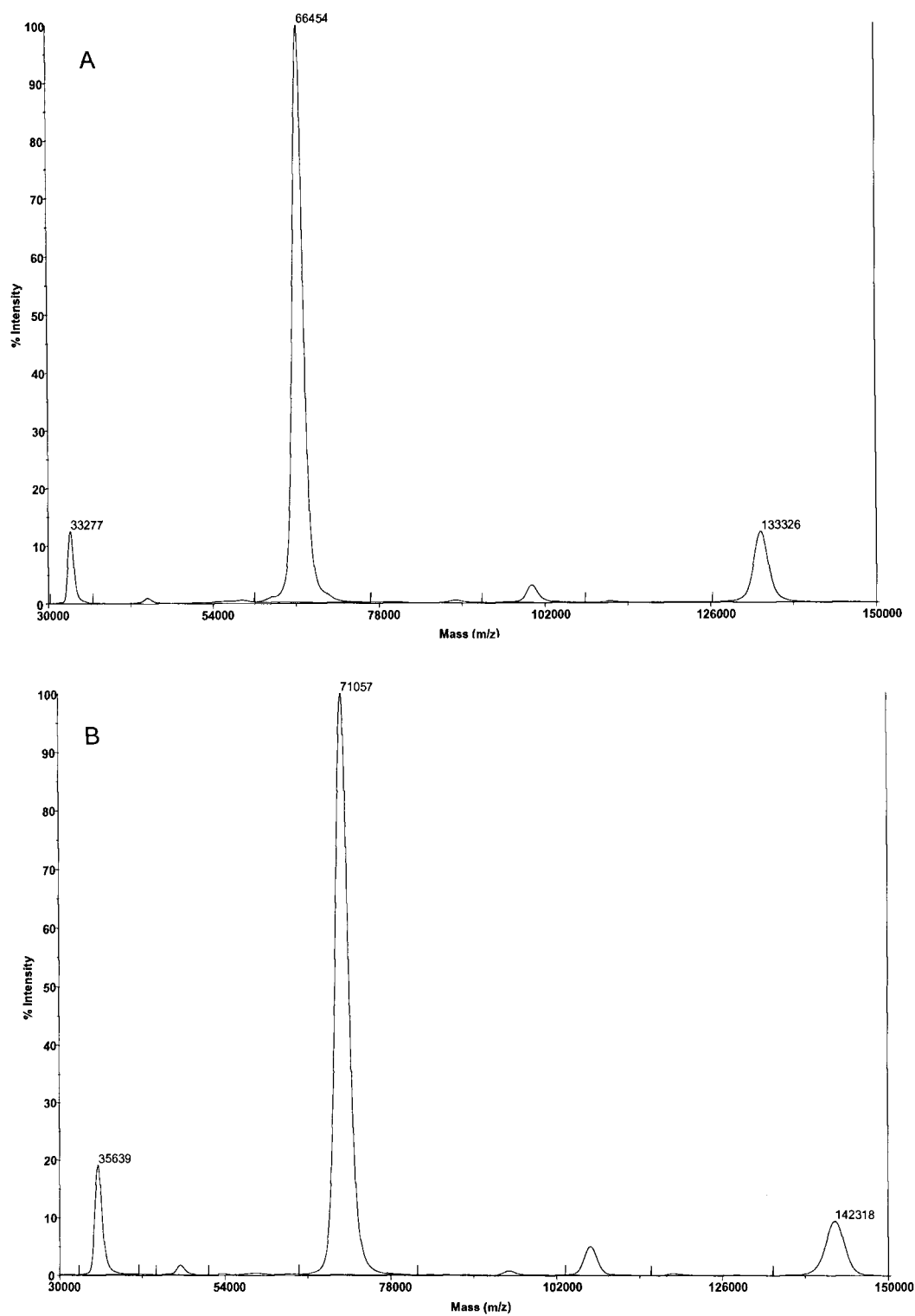
FIG. 10 shows MALDI-TOF mass spectroscopy analyses of HSA (FIG. 10A), HSA-BrAc (FIG. 10B), and HSA-BrAc-SH-LTA conjugate (FIG. 10C).
Figure 10:
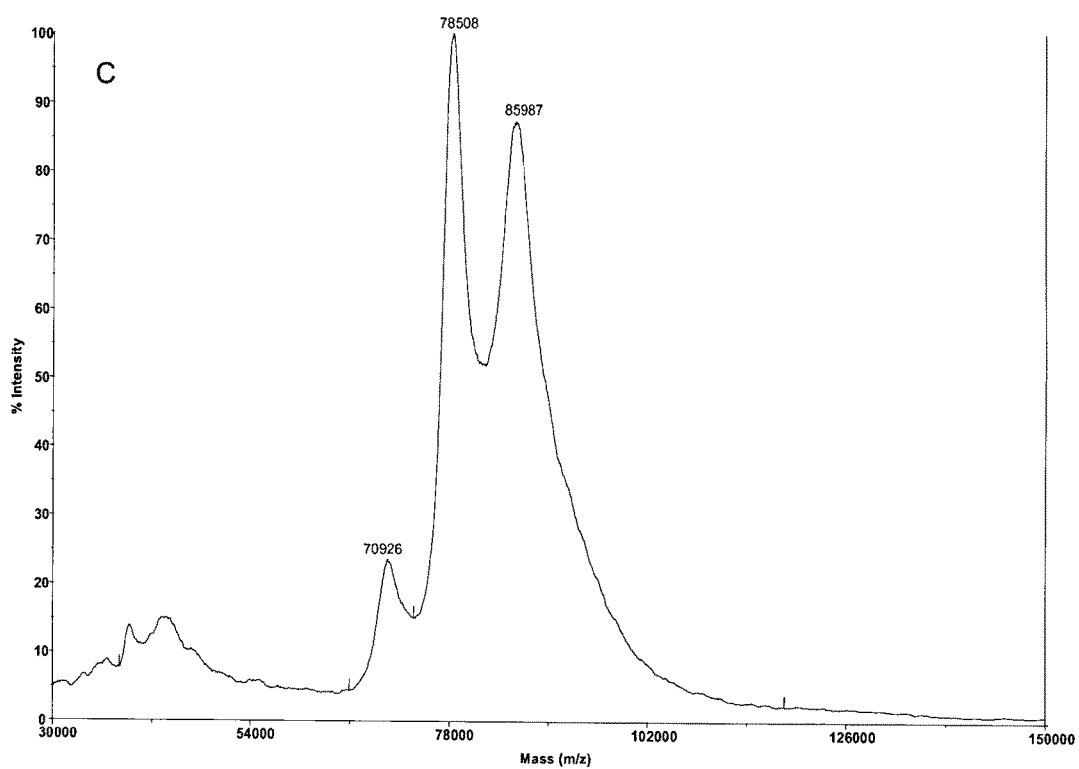

Conjugation reaction: The thiol protecting group of the carbohydrates (5 mg/ml) were removed as described above and the conditions for the conjugation reaction were the same as described above. The glycoconjugate was characterised by MALDI-TOF MS as described above. Results (FIG. 10) suggested that 1 or 2 or more carbohydrate molecules from the LTA-OH had been attached per carrier protein, and revealed a mass increase of ~7.5 kDa for each carbohydrate unit attached. This indicated that the LTA polymer attached to HSA was approximately 15 repeat units in length. The MALDI-TOF MS analysis was not as definitive for the LTA conjugate but did indicate an increase in mass from the activated protein as a result of conjugation and this was corroborated by SDS-PAGE where the conjugate was recognised by polyclonal sera raised to whole *C. difficile* cells (Example 5).

(iii) Exoprotein A (ExoA) and Maleimide (BMPH) Linker

The glycoconjugate to assess the immunogenic potential of the LTA was prepared wherein the carrier protein was Exoprotein A (ExoA) and the linker on the protein was based on maleimide (BMPH). The LTA was O-deacylated and was the linker was based on thiol (SATP).

O-deacylation and linker attachment: The purified LTA was O-deacylated and a SATP linker attached as described above.

Activation of protein carrier: In order to conjugate the protein carrier molecule ExoA to the thiol-tagged LTA, it was necessary to modify the carboxyl groups on the ExoA protein (15 mg) as described above for the HSA protein.

The activated protein was characterised by MALDI-TOF MS as described above. MALDI-TOF of activated ExoA showed that ~24 carboxyl residues had been activated with BMPH.

Conjugation reaction: The glycoconjugate was prepared as described above for the HSA-BMPH activated conjugation reaction and characterised by MALDI-TOF MS as described above. Results suggested that carbohydrate molecules had been attached per carrier protein and this was corroborated by SDS-PAGE where the conjugate migrated significantly less than the activated protein and was recognised by polyclonal sera raised to whole *C. difficile* cells (Example 5).

Example 7: Immunisation an Analysis of Derived Sera (i) Conjugate of Example 6(i)

In order to test the immunogenicity of the glycoconjugate, mice and rabbits were immunised with a prime and two booster doses of the glycoconjugate of Example 6 (i), which had been prepared from BMPH activated HSA and thiol activated de-O-acylated LTA.

Three New Zealand white rabbits (1.5-2 kg) were immunised subcutaneously with the glycoconjugate. Each rabbit received 50 µg of HSA-BMPH-SH-de-O-LTA conjugate (RCDV1-3) as 2×0.5 ml per immunisation with incomplete Freunds adjuvant for the prime immunisation and boosts. The rabbits were boosted on days 28 and 56; sera were recovered following trial bleed on day 42 and terminal heart puncture on day 70. Two rabbits also received control immunisations, which consisted of the O-deacylated carbohydrate (50 µg per rabbit (RCDC4-5)) admixed with the same amount of protein (HSA) as in the glycoconjugate and appropriate adjuvant, with the same boosting and sera recovery schedule.

Five Balb/C mice (6-8 weeks old) were also immunised intra-peritoneally with the HSA-BMPH-SH-de-O-LTA conjugate (MCDV1-5): two with 10 and three with 5 µg of conjugated carbohydrate per immunisation with Sigma adjuvant for the prime immunisation and boosts. The mice were boosted on days 21 and 42; sera were recovered following trial bleed on day 35 and terminal heart puncture on day 56. Additionally, eight mice received control immunisations, which comprised two mice (MCDC6-7) receiving O-deacylated carbohydrate (10 µg per mouse) admixed with the same amount of protein (HSA) as in the glycoconjugate, two mice (MCDC 10-11) receiving purified LTA (10 µg per mouse) admixed with the same amount of protein (HSA) as in the glycoconjugate, two mice (MCDC 8-9) receiving O-deacylated carbohydrate (10 µg per mouse) alone and two mice (MCDC 12-13) receiving native LTA (10 µg per mouse) alone, all with the same boosting and sera recovery schedule.

Whole cell ELISA was performed to determine whether sera recognized whole cells from various strains of *C. difficile*. Briefly, wells of Nunc Maxisorp EIA plates were coated with 100 µl of formalin-killed bacteria (optical density at 620 nm [OD620] of 0.080) in H$_2$O for 18 h in a 37° C. drying oven and then brought to 22-24° C. before use. Plates were blocked with 1% bovine serum albumin (BSA)-PBS for 1 h at 22-24° C., wells were washed with PBS-0.05% Tween 20 (PBS-T), and incubated with sera for 3 h at 22-24° C. Following washing with PBS-T, alkaline phosphatase-labeled goat anti-mouse IgG (or goat anti-rabbit Ig) (Cedarlane Laboratories) diluted 1:1,000 (mice) 1:3,000 (rabbits) in 1% BSA-PBS was added for 1 h at 22-24° C. The plates were then washed and developed with Phosphatase Substrate System (Kirkegaard and Perry Laboratories). After 60 min OD was measured at $A_{405nm}$ using a microtiter plate reader.

Rabbit sera were initially titrated against the homologous strain, *C. difficile* 630 which revealed good titers for sera from each conjugate immunised rabbit (Table 4). These conjugate sera were subsequently shown to be broadly cross reactive against all strains of *C. difficile* tested (Table 4) with end-point titers ranging from 1:2000 to 1:3000, compared to the two control rabbits that had end-point titers of 1:200 to 1:400, whereas sera from rabbits that received admixed de-O-acylated LTA with HSA (RCDC4-5) did not recognise the *C. difficile* strains.

Three of the five mice that received the conjugate and intriguingly two of the control mice recognised whole cells from *C. difficile* strain 630. The two control mice (mice #'s 11 and 13) which gave an IgG response to *C. difficile* strain 630 whole cells were immunised with LTA admixed with HSA (#11) or LTA alone (#13). The positive mice sera, including mice #'s 11 & 13 were subsequently shown to be broadly cross reactive against all strains of *C. difficile* that were tested (Table 6).

The reactivity of the rabbit sera was also tested against a number of other Clostridia species (Table 6) and the conjugate sera (RCDV1-3) was shown to display strong cross reactivity against *C. butyricum C. subterminales*, and *C. bifermentans* but only limited or no reactivity with *C. perfringens, C. sporogenes, C. barati* and *C. botulinum* type I and type II strains. Similarly to the testing of the *C. difficile* strains, sera from rabbits that received admixed de-O-acylated LTA with HSA (RCDC4-5) did not recognise the other Clostridial species

TABLE 6

ELISA determination of recognition of whole cells from *C. difficile* strains and other Clostridial species (as indicated) with post-immune rabbit sera (D70) and post-immune mice sera (D56) following immunisations with glycoconjugate. ELISA values after 60 min. at OD$_{405\ nm}$ are detailed. Cells were killed with formalin, washed with water and resuspended at the same OD prior to plating. Dilutions are shown in parentheses.

| *C. difficile* Strain | Conjugate Rabbit Sera (1:200) | | | | |
|---|---|---|---|---|---|
| | RCDV1 | RCDV2 | RCDV3 | RCDC4 | RCDC5 |
| Cd630 | 1.018 | 1.909 | 1.206 | 0.239 | 0.222 |
| QCD | 0.529 | 0.711 | 0.631 | 0.137 | 0.133 |
| R20291 | 0.315 | 0.503 | 0.438 | 0.114 | 0.130 |
| M120 | 0.224 | 0.321 | 0.241 | 0.076 | 0.077 |
| CM26 | 0.679 | 0.908 | 0.683 | 0.116 | 0.149 |
| 106-01 | 0.341 | 0.755 | 0.434 | 0.104 | 0.124 |
| Cd196 | 0.892 | 1.577 | 1.064 | 0.201 | 0.209 |
| 001-01 | 0.814 | 1.480 | 0.827 | 0.144 | 0.157 |
| Cd20 | 0.984 | 1.540 | 0.924 | 0.183 | 0.181 |
| B1-14 | 0.862 | 1.308 | 0.902 | 0.276 | 0.328 |
| B1-11 | 1.038 | 1.496 | 1.090 | 0.297 | 0.342 |
| B1-9 | 1.210 | 1.867 | 1.309 | 0.341 | 0.388 |
| B1-6 | 0.777 | 0.982 | 0.670 | 0.187 | 0.212 |
| CM121 | 0.429 | 0.848 | 0.418 | 0.229 | 0.216 |
| CM56 | 0.584 | 1.076 | 0.663 | 0.234 | 0.246 |
| O6CD130 | 0.848 | 0.357 | 0.988 | 0.310 | 0.269 |
| 29975 | 0.629 | 0.238 | 0.770 | 0.242 | 0.231 |
| M13876 | 0.616 | 0.985 | 0.788 | 0.203 | 0.217 |
| M16256 | 0.755 | 1.017 | 0.755 | 0.166 | 0.185 |
| B1-1 | 0.688 | 1.157 | 0.857 | 0.265 | 0.281 |
| 052694 | 0.827 | 1.164 | 0.873 | 0.220 | 0.223 |

TABLE 6-continued

ELISA determination of recognition of whole cells from C. difficile strains and other Clostridial species (as indicated) with post-immune rabbit sera (D70) and post-immune mice sera (D56) following immunisations with glycoconjugate. ELISA values after 60 min. at $OD_{405\ nm}$ are detailed. Cells were killed with formalin, washed with water and resuspended at the same OD prior to plating. Dilutions are shown in parentheses.

| C. difficile Strain | Conjugate Rabbit Sera (1:200) | | | | |
|---|---|---|---|---|---|
| | RCDV1 | RCDV2 | RCDV3 | RCDC4 | RCDC5 |
| B1-7 | 0.707 | 1.222 | 0.845 | 0.168 | 0.219 |
| M26195 | 0.682 | 1.217 | 0.895 | 0.265 | 0.255 |
| M23257 | 0.645 | 0.939 | 0.577 | 0.190 | 0.246 |
| M46846 | 0.582 | 0.898 | 0.811 | 0.202 | 0.178 |
| LIV022 | 0.298 | 0.548 | 0.352 | 0.135 | 0.186 |
| TL178 | 0.415 | 0.633 | 0.502 | 0.124 | 0.158 |
| LIV024 | 0.601 | 0.765 | 0.744 | 0.166 | 0.201 |
| TL176 | 0.512 | 0.643 | 0.493 | 0.127 | 0.141 |
| CD305 | 0.218 | 0.395 | 0.347 | 0.132 | 0.173 |
| CF5 | 0.661 | 1.008 | 0.772 | 0.182 | 0.187 |
| M6510 | 0.420 | 0.588 | 0.445 | 0.101 | 0.154 |
| TL174 | 0.353 | 0.576 | 0.442 | 0.105 | 0.149 |
| M68 | 0.252 | 0.479 | 0.329 | 0.069 | 0.078 |
| M6317 | 0.344 | 0.648 | 0.416 | 0.075 | 0.084 |
| M7465 | 0.448 | 0.711 | 0.529 | 0.102 | 0.121 |
| M9349 | 0.365 | 0.626 | 0.488 | 0.083 | 0.102 |
| M13340 | 0.539 | 0.749 | 0.518 | 0.095 | 0.099 |
| VPI 10463 | 0.779 | 1.173 | 0.698 | 0.127 | 0.145 |
| D0724491 | 0.318 | 0.330 | 0.169 | 0.191 | 0.509 |
| D0835450 | 0.446 | 0.692 | 0.424 | 0.139 | 0.674 |
| 955289 | 0.366 | 0.556 | 0.304 | 0.123 | 0.463 |
| C. perfringens | 0.255 | 0.703 | 0.233 | 0.196 | 0.224 |
| C. sporogenes | 0.180 | 0.116 | 0.146 | 0.140 | 0.162 |
| C. barati | 0.292 | 0.318 | 0.256 | 0.146 | 0.252 |
| C. butyricum | 0.606 | 0.898 | 0.586 | 0.124 | 0.183 |
| C. subterminale | 0.779 | 1.261 | 0.827 | 0.189 | 0.197 |
| C. bifermentans | 0.791 | 1.154 | 0.749 | 0.141 | 0.209 |
| C. botulinum I A6 | 0.166 | 0.213 | 0.174 | 0.132 | 0.261 |
| C. botulinum II E Russ | 0.076 | 0.057 | 0.047 | 0.083 | 0.087 |

| C. difficile Strain | Conjugate Mouse Sera (IgG 1:80) | | | | | | |
|---|---|---|---|---|---|---|---|
| | MCDV1 | MCDV2 | MCDV3 | MCDV4 | MCDV5 | MCDC11 | MCDC13 |
| Cd630 | 1.413 | 0.155 | 1.114 | 0.635 | 1.247 | 0.742 | 0.858 |
| QCD | 0.943 | 0.132 | 0.751 | 0.389 | 0.913 | 0.393 | 0.603 |
| R20291 | 0.704 | 0.123 | 0.533 | 0.304 | 0.707 | 0.261 | 0.301 |
| M68 | 0.492 | 0.092 | 0.298 | 0.174 | 0.469 | 0.177 | 0.242 |
| M120 | 0.423 | 0.081 | 0.252 | 0.152 | 0.430 | 0.175 | 0.229 |
| CM26 | 1.123 | 0.154 | 0.873 | 0.472 | 0.836 | 0.493 | 0.572 |

(ii) Conjugate of Example 6(ii)

In order to test the immunogenicity of the glycoconjugate, mice and rabbits were immunised with a prime and two booster amounts of the glycoconjugate of Example 6 (ii) which had been prepared from BrAc activated HSA and thiol activated LTA and thiol activated de-O-acylated LTA.

Six New Zealand white rabbits (1.5-2 kg) were immunised subcutaneously with the glycoconjugates. Three rabbits received 50 μg of HSA-BrAc-S H-LTA conjugate (RCLV1-3) and three rabbits received 50 μg of HSA-BrAc-SH-de-O-LTA conjugate (RCOV1-3) as 2×0.5 ml per immunisation with incomplete Freunds adjuvant for the prime immunisation and boosts. The rabbits were boosted on days 28 and 56; sera were recovered following trial bleed on day 42 and terminal heart puncture on day 70. Four rabbits also received control immunisations, which consisted of the LTA (2 rabbits RCLC4-5) or the O-deacylated LTA (2 rabbits RCOC4-5) (50 μg per rabbit) admixed with the same amount of protein (HSA) as in the glycoconjugate and appropriate adjuvant, with the same boosting and sera recovery schedule.

Ten Balb/C mice (6-8 weeks old) were also immunised intra-peritoneally with the glycoconjugates. Five mice received the HSA-BrAc-SH-LTA conjugate (MCLV 1-5) with 5 μg of conjugated carbohydrate per immunisation and five mice received the HSA-BrAc-SH-de-O-LTA conjugate (MCOV 1-5) with 5 μg of conjugated carbohydrate per immunisation with Sigma adjuvant for the prime immunisation and boosts. The mice were boosted on days 21 and 42; sera were recovered following trial bleed on day 35 and terminal heart puncture on day 56. Additionally, six mice received control immunisations, which comprised three mice receiving O-deacylated LTA (5 μg per mouse (MCOV6-8)) admixed with the same amount of protein (HSA) as in the glycoconjugate and three mice receiving the native LTA (5 μg per mouse (MCLV6-8)) admixed with the same amount of protein (HSA) as in the glycoconjugate, all with the same boosting and sera recovery schedule.

Whole cell ELISA was performed to determine whether sera recognized whole cells from various strains of C. difficile as described above.

Rabbit sera were initially titrated against the homologous strain, C. difficile 630, which revealed good titers for sera from each LTA conjugate immunised rabbit (RCLV1-3) and generally weaker titers for the de-0 LTA conjugate immunised rabbits (RCOV1-3). Intriguingly the control rabbits that received LTA admixed with HSA (RCLC4-5) also recognised the C. difficile 630 whole cells. The sera that were generated to LTA containing immunogens, either conjugated or free LTA, were subsequently shown to be broadly cross reactive against all strains of C. difficile tested (Table 7). Generally speaking the de-O-LTA conjugate derived sera (RCOV1-3) and the de-O-LTA admixed with HSA derived sera (RCOC4-5) recognised the majority of the C. difficile cells at lower titers than the LTA immunogen derived sera.

The reactivity of the rabbit sera was also tested against a number of other Clostridial species (Table 7). Serum from rabbits immunised with either LTA conjugate (RCLC1-3) or LTA admixed with HSA (RCLC4-5) all generated antibodies which reacted against C. butyricum C. subterminales and C. bifermentans but not with C. perfringens, C. sporogenes C. barati and C. botulinum type I and type II strains.

TABLE 7

ELISA determination of recognition of whole cells from C. difficile strains and other Clostridial species (as indicated) with post-immune rabbit sera (D70) following immunisations with glycoconjugate. ELISA values after 60 min. at $OD_{405\ nm}$ are detailed. Dilutions are shown in parentheses.

| C. difficile Strain | Conjugate Rabbit Sera (1:200) | | | | |
| --- | --- | --- | --- | --- | --- |
| | RCOV1 | RCOV2 | RCOV3 | RCOC4 | RCOC5 |
| Cd630 | 0.598 | 2.651 | 1.181 | 0.772 | 0.261 |
| QCD | 1.232 | 0.228 | 0.308 | 0.436 | 0.149 |
| R20291 | 0.906 | 0.158 | 0.276 | 0.487 | 0.181 |
| M120 | 0.547 | 0.189 | 0.194 | 0.375 | 0.134 |
| CM26 | 1.271 | 0.394 | 0.445 | 0.454 | 0.191 |
| 106-01 | 0.218 | 1.190 | 0.340 | 1.106 | 0.323 |
| Cd196 | 0.464 | 2.188 | 0.281 | 0.964 | 0.313 |
| 001-01 | 0.403 | 2.294 | 0.290 | 1.126 | 0.325 |
| Cd20 | 0.454 | 2.291 | 0.295 | 1.118 | 0.323 |
| B1-14 | 0.636 | 1.581 | 0.411 | 1.097 | 0.396 |
| B1-11 | 0.696 | 1.701 | 0.419 | 1.424 | 0.498 |
| B1-9 | 0.820 | 1.938 | 0.455 | 0.692 | 0.286 |
| B1-6 | 0.411 | 1.182 | 0.410 | 0.777 | 0.313 |
| CM121 | 0.326 | 0.965 | 0.508 | 0.891 | 0.274 |
| CM56 | 0.406 | 1.363 | 0.319 | 0.909 | 0.311 |
| O6CD130 | 0.657 | 1.708 | 0.486 | 0.743 | 0.265 |
| 29975 | 0.633 | 1.580 | 0.840 | 0.737 | 0.286 |
| M13876 | 0.454 | 1.311 | 0.270 | 0.865 | 0.308 |
| M16256 | 0.468 | 1.291 | 0.315 | 0.895 | 0.342 |
| B1-1 | 0.592 | 1.601 | 0.317 | 0.908 | 0.297 |
| 052694 | 0.397 | 1.429 | 0.284 | 0.878 | 0.318 |
| B1-7 | 0.497 | 1.450 | 0.341 | 0.764 | 0.295 |
| M26195 | 0.437 | 1.633 | 0.340 | 0.867 | 0.302 |
| M23257 | 0.439 | 1.112 | 0.272 | 0.618 | 0.274 |
| M46846 | 0.425 | 1.036 | 0.687 | 0.444 | 0.212 |
| LIV022 | 0.310 | 0.989 | 0.247 | 0.460 | 0.161 |
| TL178 | 0.336 | 0.895 | 0.230 | 0.363 | 0.137 |
| LIV024 | 0.438 | 1.013 | 0.234 | 0.466 | 0.193 |
| TL176 | 0.289 | 0.850 | 0.508 | 0.384 | 0.159 |
| CD305 | 0.893 | 0.180 | 0.227 | 0.603 | 0.207 |
| CF5 | 1.244 | 0.403 | 0.417 | 0.670 | 0.206 |
| M6510 | 1.032 | 0.307 | 0.683 | 0.600 | 0.222 |
| TL174 | 0.960 | 0.146 | 0.318 | 0.679 | 0.305 |
| M68 | 0.222 | 0.717 | 0.303 | 0.363 | 0.136 |
| M6317 | 0.254 | 1.004 | 0.203 | 0.322 | 0.137 |
| M7465 | 0.335 | 1.003 | 0.250 | 0.326 | 0.146 |
| M9349 | 0.249 | 0.948 | 0.170 | 0.287 | 0.108 |
| M13340 | 0.263 | 1.048 | 0.211 | 0.289 | 0.125 |
| VPI 10463 | 0.419 | 1.442 | 0.287 | 0.744 | 0.242 |
| D0724491 | 0.232 | 0.578 | 0.267 | 0.659 | 0.276 |
| D0835450 | 0.305 | 1.135 | 0.280 | 0.674 | 0.270 |
| 955289 | 0.240 | 0.799 | 0.224 | 0.654 | 0.249 |
| C. perfringens | 0.268 | 0.392 | 0.268 | 0.824 | 0.341 |
| C. sporogenes | 0.166 | 0.314 | 0.195 | 0.873 | 0.324 |
| C. barati | 0.349 | 0.438 | 0.293 | 0.760 | 0.479 |
| C. butyricum | 0.319 | 1.212 | 0.292 | 0.639 | 0.285 |
| C. subterminale | 0.447 | 1.548 | 0.288 | 0.777 | 0.292 |
| C. bifermentans | 0.484 | 1.497 | 0.358 | 0.692 | 0.272 |
| C. botulinum A6 | 0.342 | 0.410 | 0.212 | 0.742 | 0.301 |
| C. botulinum II E Russ | 0.064 | 0.121 | 0.112 | 0.490 | 0.143 |

| C. difficile Strain | Conjugate Rabbit Sera (1:200) | | | | |
| --- | --- | --- | --- | --- | --- |
| | RCLV1 | RCLV2 | RCLV3 | RCLC4 | RCLC5 |
| Cd630 | 1.263 | 2.577 | 2.376 | 1.348 | 2.649 |
| QCD | 0.303 | 0.866 | 0.817 | 0.495 | 0.769 |
| R20291 | 0.202 | 0.638 | 0.532 | 0.360 | 0.704 |
| M120 | 0.092 | 0.465 | 0.550 | 0.330 | 0.501 |
| CM26 | 0.389 | 0.885 | 0.826 | 0.662 | 0.954 |
| 106-01 | 0.235 | 1.031 | 0.794 | 0.464 | 1.166 |
| Cd196 | 0.491 | 2.067 | 1.627 | 0.803 | 2.176 |
| 001-01 | 0.539 | 2.202 | 1.844 | 1.088 | 2.409 |
| Cd20 | 0.611 | 2.251 | 1.855 | 1.145 | 2.409 |
| B1-14 | 0.610 | 1.349 | 1.181 | 0.830 | 1.253 |
| B1-11 | 0.776 | 1.821 | 1.620 | 0.997 | 1.629 |
| B1-9 | 0.336 | 0.800 | 0.775 | 0.636 | 1.132 |
| B1-6 | 0.552 | 1.185 | 1.044 | 0.763 | 1.415 |
| CM121 | 0.280 | 0.676 | 0.986 | 0.500 | 0.779 |
| CM56 | 0.471 | 1.314 | 1.254 | 0.843 | 1.487 |
| O6CD130 | 0.528 | 1.336 | 1.203 | 0.923 | 1.235 |
| 29975 | 0.839 | 1.519 | 1.444 | 0.866 | 1.328 |
| M13876 | 0.463 | 1.226 | 1.255 | 0.738 | 0.969 |
| M16256 | 0.449 | 1.107 | 1.150 | 0.678 | 1.242 |
| B1-1 | 0.388 | 1.205 | 1.231 | 0.753 | 1.075 |
| 052694 | 0.479 | 1.320 | 1.152 | 0.864 | 1.343 |
| B1-7 | 0.484 | 1.012 | 0.947 | 0.768 | 1.014 |
| M26195 | 0.401 | 1.480 | 1.378 | 0.831 | 1.586 |
| M23257 | 0.479 | 1.015 | 0.876 | 0.582 | 1.142 |
| M46846 | 0.735 | 1.174 | 1.108 | 0.590 | 0.936 |
| LIV022 | 0.171 | 0.755 | 0.704 | 0.298 | 0.697 |
| TL178 | 0.257 | 0.936 | 0.760 | 0.364 | 0.857 |
| LIV024 | 0.340 | 0.981 | 0.901 | 0.606 | 1.012 |
| TL176 | 0.302 | 1.004 | 0.925 | 0.490 | 0.841 |
| CD305 | 0.136 | 0.573 | 0.449 | 0.239 | 0.503 |
| CF5 | 0.616 | 1.000 | 0.923 | 0.609 | 1.073 |
| M6510 | 0.512 | 1.014 | 1.005 | 0.492 | 0.937 |
| TL174 | 0.308 | 0.872 | 0.658 | 0.461 | 0.912 |
| M68 | 0.131 | 0.408 | 0.405 | 0.249 | 0.489 |
| M6317 | 0.191 | 0.758 | 0.637 | 0.337 | 0.702 |
| M7465 | 0.290 | 0.721 | 0.686 | 0.485 | 0.851 |
| M9349 | 0.164 | 0.674 | 0.595 | 0.363 | 0.766 |
| M13340 | 0.285 | 0.763 | 0.729 | 0.505 | 0.833 |
| VPI 10463 | 0.387 | 1.256 | 1.150 | 0.696 | 1.144 |
| D0724491 | 0.200 | 0.422 | 0.427 | 0.258 | 0.557 |
| D0835450 | 0.228 | 0.889 | 0.884 | 0.398 | 0.834 |
| 955289 | 0.168 | 0.655 | 0.595 | 0.276 | 0.693 |
| C. perfringens | 0.503 | 0.328 | 0.507 | 0.541 | 0.365 |
| C. sporogenes | 0.163 | 0.313 | 0.300 | 0.247 | 0.310 |
| C. barati | 0.237 | 0.261 | 0.218 | 0.337 | 0.530 |
| C. butyricum | 0.331 | 1.101 | 0.971 | 0.584 | 1.025 |
| C. subterminale | 0.473 | 1.268 | 1.132 | 0.833 | 1.264 |
| C. bifermentans | 0.432 | 1.235 | 1.075 | 0.756 | 1.318 |
| C. botulinum A6 | 0.120 | 0.374 | 0.209 | 0.237 | 0.506 |
| C. botulinum E Russ | 0.057 | 0.111 | 0.088 | 0.097 | 0.155 |

(iii) Conjugate of Example 6(iii)

In order to test the immunogenicity of the glycoconjugate, mice and rabbits were immunised with a prime and two booster amounts of the glycoconjugate of Example 6 (iii) which had been prepared from BMPH activated ExoA and thiol activated de-O-acylated LTA.

Three New Zealand white rabbits (1.5-2 kg) were immunised subcutaneously with the glycoconjugates receiving 25 µg of ExoA-BMPH-SH-de-O-LTA conjugate (RCXV 1-3) as 2×0.5 ml per immunisation with incomplete Freunds adjuvant for the prime immunisation and boosts. The rabbits were boosted on days 28 and 56; sera were recovered following trial bleed on day 42 and terminal heart puncture on day 70. Two rabbits also received control immunisations, which consisted of the O-deacylated LTA (50 µg per rabbit (RCXC 4-5)) admixed with the same amount of protein (ExoA) as in the glycoconjugate and appropriate adjuvant, with the same boosting and sera recovery schedule.

Five Balb/C mice (6-8 weeks old) were also immunised intra-peritoneally with the glycoconjugates (MCXV 1-5) receiving the ExoA-BMPH-SH-de-O-LTA conjugate with 5 µg of conjugated carbohydrate per immunisation with Sigma adjuvant or the prime immunisation and boosts. The mice were boosted on days 21 and 42; sera were recovered following trial bleed on day 35 and terminal heart puncture on day 56. Additionally, three mice received control immunisations, which comprised of receiving O-deacylated LTA (5 µg per mouse (MCXC 6-8)) admixed with the same amount of protein (ExoA) as in the glycoconjugate, all with the same boosting and sera recovery schedule.

Whole cell ELISA was performed to determine whether sera recognized whole cells from various strains of *C. difficile* as described above.

Rabbit sera were initially titrated against the homologous strain, *C. difficile* 630 which revealed good titers for sera from each conjugate immunised rabbit (RCXV1-3) (Table 8). These sera were subsequently shown to be broadly cross reactive against all strains of *C. difficile* tested (Table 8) compared to the two control rabbits (RCXC4-5) which only received the de-O-acylated LTA admixed with ExoA.

All of the five mice that received the conjugate (MCXV1-5) and none of the control mice (MCXC6-8) recognised whole cells from *C. difficile* strain 630. The positive mice sera were subsequently shown to be broadly cross reactive against all strains of *C. difficile* that were tested (Table 8).

The reactivity of the rabbit sera was also tested against a number of other Clostridial species (Table 8) and only the LTA conjugate antisera (RCXV1-3) was shown to display strong cross reactivity against *C. butyricum, C. subterminales* and *C. bifermentans*. No reactivity was observed with *C. perfringens, C. sporogenes C. barati* and *C. botulinum* type I and type II strains with the conjugate serum. Control sera from rabbits which received the de-O-acylated LTA admixed with ExoA (RCXC 4-5) did not exhibit any cross reactivity with other Clostridial species.

TABLE 8

ELISA determination of recognition of whole cells from *C. difficile* strains and other Clostridial species (as indicated) with post-immune rabbit sera (D70) and post-immune mice sera (D56) following immunisations with glycoconjugate. ELISA values after 60 min. at $OD_{405\ nm}$ are detailed. Dilutions are shown in parentheses.

| *C. difficile* Strain | Conjugate Rabbit Sera (1:200) | | | | |
|---|---|---|---|---|---|
| | RCXV1 | RCXV2 | RCXV3 | RCXC4 | RCXC5 |
| Cd630 | 0.997 | 1.008 | 0.877 | 0.106 | 0.229 |
| QCD | 1.265 | 1.194 | 1.009 | 0.075 | 0.152 |
| R20291 | 1.353 | 1.319 | 1.109 | 0.061 | 0.132 |
| M120 | 1.041 | 1.034 | 0.878 | 0.056 | 0.127 |
| CM26 | 1.435 | 1.234 | 1.015 | 0.069 | 0.145 |
| 106-01 | 1.350 | 1.303 | 1.148 | 0.063 | 0.152 |
| Cd196 | 1.694 | 1.507 | 1.469 | 0.159 | 0.819 |
| 001-01 | 1.540 | 1.456 | 1.454 | 0.122 | 0.661 |
| Cd20 | 1.803 | 1.659 | 1.463 | 0.192 | 0.754 |
| B1-14 | 1.508 | 1.432 | 1.208 | 0.115 | 0.151 |
| B1-11 | 1.668 | 1.552 | 1.330 | 0.140 | 0.209 |
| B1-9 | 1.586 | 1.369 | 1.261 | 0.132 | 0.162 |
| B1-6 | 1.813 | 1.682 | 1.646 | 0.130 | 0.177 |
| CM121 | 1.138 | 1.158 | 0.980 | 0.040 | 0.122 |
| CM56 | 1.569 | 1.449 | 1.322 | 0.125 | 0.240 |
| O6CD130 | 1.442 | 1.392 | 1.365 | 0.083 | 0.291 |
| 29975 | 1.687 | 1.526 | 1.494 | 0.156 | 0.308 |
| M13876 | 1.423 | 1.339 | 1.275 | 0.121 | 0.119 |
| M16256 | 1.417 | 1.375 | 1.330 | 0.120 | 0.120 |
| B1-1 | 1.742 | 1.628 | 1.563 | 0.118 | 0.158 |
| 052694 | 1.582 | 1.593 | 1.462 | 0.140 | 0.187 |
| B1-7 | 1.726 | 1.646 | 1.614 | 0.122 | 0.578 |
| M26195 | 1.542 | 1.460 | 1.361 | 0.223 | 0.128 |
| M23257 | 1.592 | 1.618 | 1.693 | 0.176 | 0.702 |
| M46846 | 1.779 | 1.591 | 1.437 | 0.163 | 0.601 |
| LIV022 | 1.495 | 1.468 | 1.298 | 0.178 | 0.122 |
| TL178 | 1.372 | 1.232 | 1.116 | 0.055 | 0.050 |
| LIV024 | 1.760 | 1.431 | 1.393 | 0.101 | 0.161 |
| TL176 | 1.551 | 1.342 | 1.218 | 0.117 | 0.079 |
| CD305 | 0.679 | 0.711 | 0.626 | 0.025 | 0.040 |
| CF5 | 1.620 | 1.481 | 1.326 | 0.084 | 0.124 |
| M6510 | 1.327 | 1.084 | 1.024 | 0.072 | 0.110 |
| TL174 | 1.330 | 1.193 | 1.000 | 0.040 | 0.039 |
| M68 | 1.044 | 1.045 | 0.870 | 0.057 | 0.144 |
| M6317 | 1.283 | 1.290 | 1.023 | 0.062 | 0.070 |
| M7465 | 1.456 | 1.200 | 1.125 | 0.088 | 0.086 |
| M9349 | 1.352 | 1.245 | 1.148 | 0.074 | 0.068 |
| M13340 | 1.443 | 1.359 | 1.160 | 0.098 | 0.169 |
| VPI 10463 | 2.043 | 1.734 | 1.358 | 0.116 | 0.134 |
| D0724491 | 0.917 | 0.949 | 0.813 | 0.153 | 0.153 |
| D0835450 | 1.375 | 1.232 | 1.081 | 0.135 | 0.104 |
| 955289 | 1.214 | 1.215 | 1.064 | 0.178 | 0.097 |
| *C. perfringens* | 0.216 | 0.957 | 0.307 | 0.157 | 0.171 |
| *C. sporogenes* | 0.137 | 0.153 | 0.202 | 0.128 | 0.149 |
| *C. barati* | 0.230 | 0.272 | 0.411 | 0.178 | 0.176 |
| *C. butyricum* | 1.818 | 1.672 | 1.549 | 0.104 | 0.129 |
| *C. subterminale* | 1.884 | 1.697 | 1.458 | 0.131 | 0.134 |
| *C. bifermentans* | 1.674 | 1.466 | 1.309 | 0.129 | 0.140 |
| *C. botulinum* A6 | 0.138 | 0.191 | 0.290 | 0.111 | 0.152 |
| *C. botulinum* E Russ | 0.053 | 0.064 | 0.096 | 0.045 | 0.047 |

| C. difficile | Conjugate Mouse Sera (IgG 1:80) | | | | | | | |
|---|---|---|---|---|---|---|---|---|
| Strain | MCXV1 | MCXV2 | MCXV3 | MCXV4 | MCXV5 | MCXC6 | MCXC7 | MCXC8 |
| Cd630 | 0.643 | 1.625 | 1.377 | 0.987 | 0.932 | 0.036 | 0.043 | 0.140 |
| QCD | 0.395 | 1.480 | 1.187 | 0.714 | 0.637 | 0.040 | 0.056 | 0.151 |
| R20291 | 0.275 | 1.190 | 0.827 | 0.470 | 0.368 | 0.032 | 0.037 | 0.106 |
| M68 | 0.182 | 1.033 | 0.622 | 0.345 | 0.292 | 0.022 | 0.027 | 0.077 |
| M120 | 0.182 | 0.638 | 0.703 | 0.356 | 0.283 | 0.025 | 0.040 | 0.064 |
| CM26 | 0.418 | 1.296 | 1.013 | 0.665 | 0.638 | 0.026 | 0.070 | 0.122 |

Example 8: Immunofluorescence at Bacterial Cell Surface

In order to determine if antibodies in immune serum could access LTA epitopes on bacterial cell surface, immunofluorescence on live *C. difficile* vegetative cells was performed.

*C. difficile* was cultured to mid-log phase in BHI broth without shaking in a MiniMacs anaerobic chamber at 37° C. The cells were centrifuged to remove the broth, re-suspended in PBS, then 10 µl was air dried onto glass coverslips. The bacteria were heat fixed to the coverslip by passing though a bunsen flame 5-6 times, then were blocked with 5% milk-PBS for 30 minutes at room temperature. The cells were incubated for 45 minutes at room temperature in 50 µl of either the pre- or post-immune anti-LTA serum at a dilution of 1:100 in PBS. The coverslips were washed with PBS then incubated for 45 minutes at room temperature with 50 µl goat anti-rabbit IgG Alexafluor 488 FITC antibody (Invitrogen, Eugene, Oreg., USA) at a 1:1000 dilution. The coverslips were washed with PBS, mounted with Vectashield-DAPI (Vector Laboratories, Burlington, Canada) then examined with a Zeiss microscope (Axiovert 200M).

Results of immunofluorescence experiments using pre or post immune serum from rabbits RCDV2, RCLV2 and RCXV2 with live whole cells of *C. difficile* are shown in Table 9. The accessibility to the cell surface and cross reactivity to vegetative cells of strains 630, R20291 and QCD32g58 is demonstrated by the binding activity of the post immune serum. No fluorescence was observed with any of the strains when pre-immune serum was used. This illustrates that the derived sera is specifically recognising a conserved accessible epitope on the surface of live *C. difficile* vegetative cells.

TABLE 9

Cell surface reactivity of LTA conjugate sera by immunofluorescence imaging

| C. difficile | RCDV2 | | RCLV2 | | RCXV2 | |
|---|---|---|---|---|---|---|
| strain (cell type) | Pre immune | Post immune | Pre immune | Post immune | Pre immune | Post immune |
| 630 (vegetative) | − | + | − | + | − | + |
| QCD32g58 (vegetative) | − | + | − | + | − | + |
| R20291 (vegetative) | − | + | − | + | − | + |
| 630 (spore) | − | + | ND | ND | − | + |
| R20291 (spore) | − | + | ND | ND | − | + |

*ND not determined, − cells no reactivity, + cells reactive.

Example 9: Immunofluorescence of *C. difficile* Spores

In order to determine if antibodies in immune serum would react with *C. difficile* spore surface, immunofluorescence on *C. difficile* spores was performed as described in Example 8.

*C. difficile* was cultured on BHI agar plates in a MiniMacs anaerobic chamber at 37° C. for 7 days to allow spore formation. Spores were purified by heat inactivating any vegetative cells for 20 minutes at 60° C. then by multiple washes in ice cold $H_2O$. Once purified, 10 µl of spores was air dried onto glass coverslips. The bacterial spore preparation was heat fixed to the coverslip by passing though a bunsen flame 5-6 times, then were blocked with 5% milk-PBS for 30 minutes at room temperature. The cells were incubated for 45 minutes at room temperature in 50 µl of either the pre- or post-immune anti-LTA serum at a dilution of 1:100 in PBS. The coverslips were washed with PBS then incubated for 45 minutes at room temperature with 50 µl goat anti-rabbit IgG Alexafluor 488 FITC antibody (Invitrogen, Eugene, Oreg., USA) at a 1:1000 dilution. The coverslips were washed with PBS, mounted with Vectashield-DAPI (Vector Laboratories, Burlington, Canada) then examined with a Zeiss microscope (Axiovert 200M).

Results are shown in Table 9. Spores are shown to bind with the RCDV2 and RCXV2 immune sera. No binding was observed when pre-immune serum was used. This may allow the use of immune LTA sera as a means to identify spores of *C. difficile*.

Example 10: Opsonophagocytic Activity Against *C. difficile* Cells

In order to determine if antibodies in immune serum had opsonizing activity and facilitated uptake by phagocytic cells, opsonophagocytic assays were performed with a THP-1 monocyte cell line.

THP-1 Cell Culture Conditions

THP-1 monocyte cells were grown in RPMI-1640 with 2 mM L-glutamine, 10% FBS and gentamicin. Cells are propagated at a density between $1\times10^5$ cells/ml and $1\times10^6$ cells/ml, with media changes every 3-4 days. For differentiation, cells are suspended in media at a density of $5\times10^5$ cells/ml, containing 200 nM Phorbol myristate acetate (PMA). For experiments in a 24-well plate, 0.5 ml of cell suspension is added per well, for a total of $2.5\times10^5$ cells/well. THP-1 cells are allowed to differentiate for 24 hours, at which time the PMA containing media is removed and replaced with fresh RPMI-1640+10% FBS and allowed to rest for a further 24 hours before use in the opsonophagocytosis assay.

Bacterial Opsonisation

*C. difficile* 630 cells were grown in BHI supplemented broth to an $OD_{600}$ of 1.0. Bacteria (5 ml) were harvested by centrifugation and washed with 5 ml PBS and resuspended to cell concentration of $1 \times 10^8$ cells/ml. For opsonization, 0.5 ml of cell suspension was mixed with 500 ul serum (heat inactivated) at appropriate dilution in PBS (1:10 or 1:100) and incubated in anaerobic chamber for 30 min. This suspension was either used directly in opsonophagocytosis assay or the opsonised bacteria were collected by centrifugation and resuspended in PBS and then used in the assay. Serum used—CD1, unrelated antisera, RCXV2.

Opsonophagocytic Assay

To determine opsonophagocytic activity, THP-1 cells at concentration of $2.5 \times 10^5$ cells/well (24 well tissue culture plate) were washed with 3×1 ml PBS to remove undifferentiated cells and then THP-1 cells were incubated with opsonised bacterial suspension for 30 min at 37° C. under aerobic conditions. The THP monolayer was then washed 3×1 ml PBS. THP cells were lysed by addition of 1 ml of cold $dH_2O$ and mixing by pipetting. Serial dilutions of each well were prepared in PBS and samples plated on Braziers agar and incubated 24 h in anaerobic chamber and bacterial colonies counted to determine the opsonizing activity of each serum.

TABLE 10

Opsonising activity of *C. difficile* 630 (CD1) whole cell rabbit polyclonal antisera

| Test condition | Expt 1 CFU count | Expt 2 CFU count | Expt 3 CFU count |
|---|---|---|---|
| THP + CD630 cells + CD1 serum (1/100) | 51000 | 309000 | 231000 |
| THP + CD630 cells + unrelated serum (1/100) | 10 | 300 | 400 |

Fluorescence Imaging of Bacteria Captured by Opsonophagocytosis.

THP monocytes were cultured on coverslips in 24 well plates. After completion of the opsonophagocytic assay as described above the wells were washed three times with 1 ml PBS then were fixed with 3% formalin at 4° C. overnight. Then each well was washed with PBS, and the coverslips removed and incubated at room temperature with 1:100 dilution of rabbit polyclonal antiserum to *C. difficile* 630 cells in PBS for 45 minutes. The coverslips were washed with PBS then incubated with 1:1000 dilution of Alexafluor 488 anti rabbit IgG (Invitrogen) in PBS at room temperature for 45 minutes. The coverslips were washed in PBS then permeabilised with 0.1% Triton in PBS for 15 minutes at room temperature followed by washing in PBS and incubation in a 1:100 dilution of rabbit polyclonal antiserum to *C. difficile* 630 cells at room temperature for 45 minutes. After washing in PBS, the coverslips were incubated in a 1:800 dilution of Alexafluor 594 anti rabbit IgG (Invitrogen) in PBS for 45 minutes at room temperature then washed in PBS and mounted onto slides with Vectashield+DAPI (Vector Laboratories) and examined with Axiovert 200M (Zeiss) microscope. Internalised and surface bound bacteria were identified by differential staining (red internalised, green surface associated). Higher numbers of bacteria were shown by immunofluorescence to associate with and be internalised by THP monocytes when CD1 antiserum was used (1:100) when compared to the unrelated antiserum control.

The embodiments and examples described herein are illustrative and are not meant to limit the scope of the invention as claimed. Variations of the foregoing embodiments, including alternatives, modifications and equivalents, are intended by the inventors to be encompassed by the claims. Furthermore, the discussed combination of features might not be necessary for the inventive solution.

The invention claimed is:

1. A composition comprising an LTA compound comprising the structure of Formula I

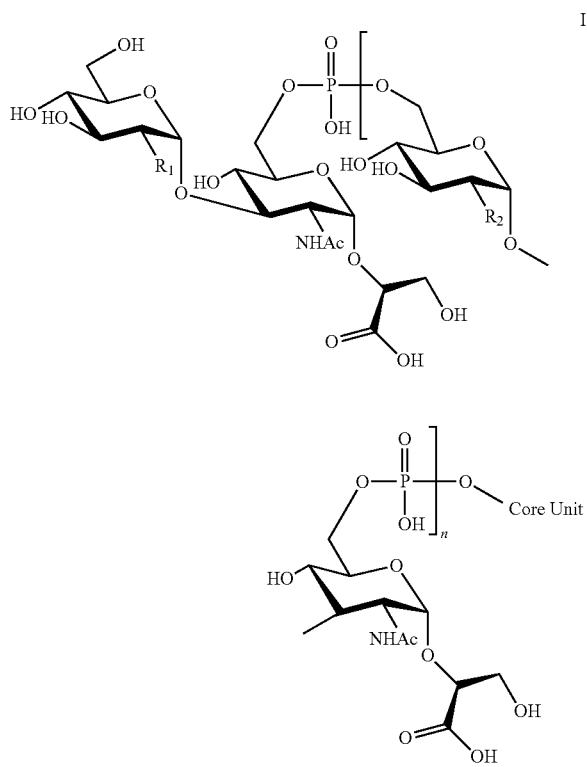

I wherein $R_1$ is selected from $NH_2$ and NHAc; each $R_2$ is independently selected from $NH_2$ and NHAc; and n is an integer between about 1 and 20, wherein the compound is covalently-linked to a carrier molecule.

2. The composition of claim 1, wherein the degree of acetylation of the LTA compound is in the range of about 65 to 100%.

3. The composition of claim 2, wherein the degree of acetylation of the LTA compound is about 65-75%.

4. The composition of claim 1, wherein n is between 12 and 16.

5. The composition of claim 1, wherein the percentage of de-acetylation in the LTA compound is about 30%.

6. The composition of claim 1, wherein the core unit comprises three glucose (Glcp) residues and a glycerol (Gro) residue.

7. The composition of claim 6, wherein the core unit comprises the structure of Formula II

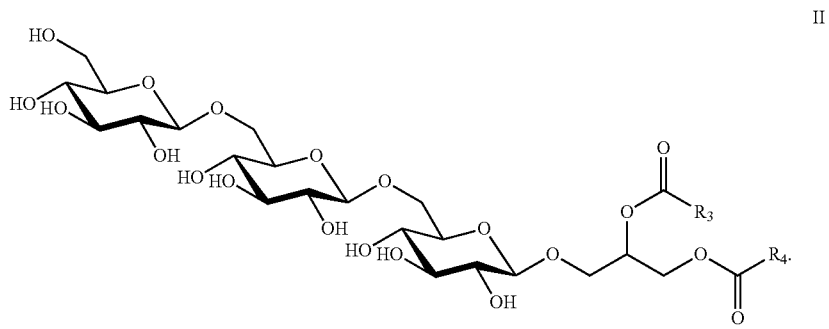

II wherein $R_3$ and $R_4$ are independently selected from a C14:0, C16:0, C16:1, C18:0, or C18:1 fatty acid, or any combination thereof and wherein one of $COR_3$ or $COR_4$ may be replaced by H.

8. The composition of claim 1, wherein the LTA compound comprises the structure of Formula III

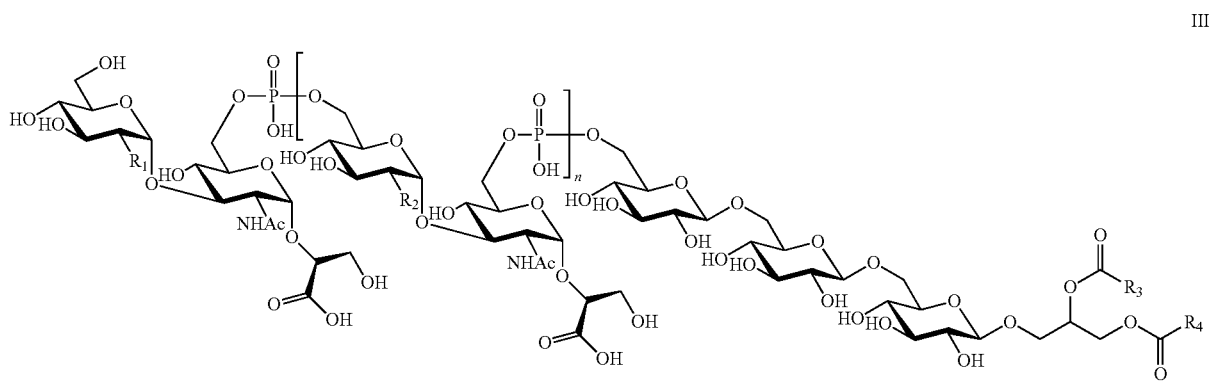

III wherein $R_1$ is selected from $NH_2$ and NHAc; each $R_2$ is independently selected from $NH_2$ and NHAc; n is an integer between about 1 and 20; $R_3$ and $R_4$ are independently selected from a C14:0, C16:0, C16:1, C18:0, or C18:1 fatty acid, or any combination thereof and wherein one of $COR_3$ or $COR_4$ may be replaced by H.

9. The composition of claim 8, wherein the LTA compound comprises the structure of Formula IV:

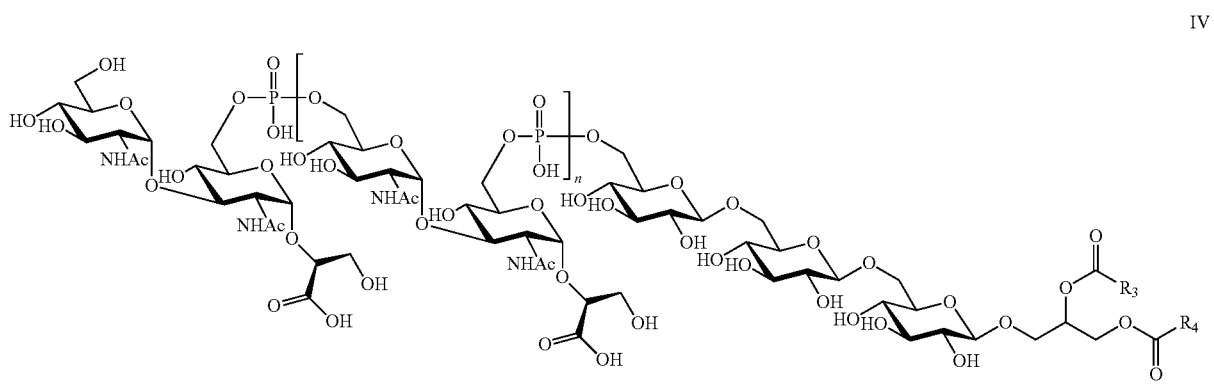

IV wherein n is an integer between 1 and 20, $R_3$ and $R_4$ are independently selected from a C14:0, C16:0, C16:1, C18:0, or C18:1 fatty acid or any combination thereof and wherein one of $COR_3$ or $COR_4$ may be replaced by H.

10. The composition of claim 1, wherein the carrier molecule is selected from the group consisting of a peptide, a protein, a membrane protein, a carbohydrate moiety, and one or more liposomes loaded with any of the previous carrier molecules.

11. An immunogenic composition comprising the composition of claim 1.

12. The immunogenic composition of claim 11, further comprising an effective amount of an adjuvant.

13. The composition of claim 1, further comprising a pharmaceutically acceptable diluent, carrier, or excipient.

14. The composition of claim 1, further comprising an adjuvant.

15. An immunogenic composition comprising an isolated LTA compound comprising a structure of Formula I 19. The immunogenic composition of claim 15, wherein the percentage of de-acetylation in the LTA compound is about 30%.

20. The immunogenic composition of claim 15, wherein the carbohydrate residues are further substituted by D-Ala, phosphorylcholine, or by a sugar.

21. The immunogenic composition of claim 15, wherein the core unit comprises three glucose (Glcp) residues and a glycerol (Gro) residue.

22. The immunogenic composition of claim 15, wherein the core unit comprises the structure of Formula II

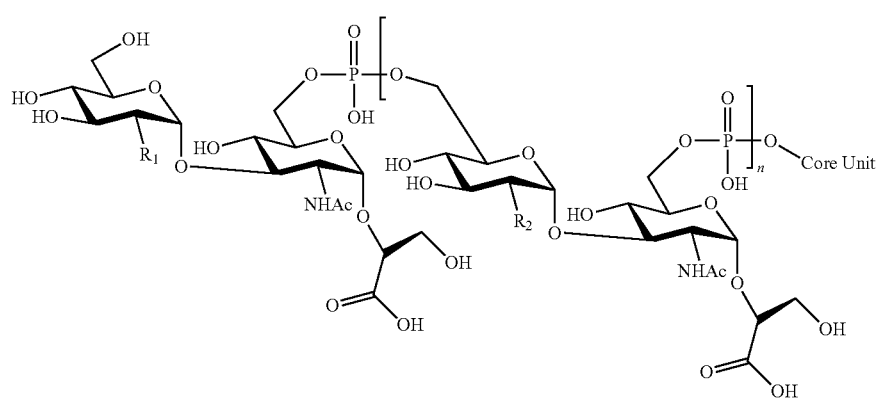

I wherein $R_1$ is selected from $NH_2$ and NHAc; each $R_2$ is independently selected from $NH_2$ and NHAc; and n is an integer between about 1 and 20, and an immuno-effective amount of an adjuvant.

16. The immunogenic composition of claim 15, wherein the degree of acetylation of the LTA compound is in the range of about 65 to 100%.

17. The immunogenic composition of claim 15, wherein the degree of acetylation of the LTA compound is about 65-75%.

18. The immunogenic composition of claim 15, wherein n is between 12 and 16.

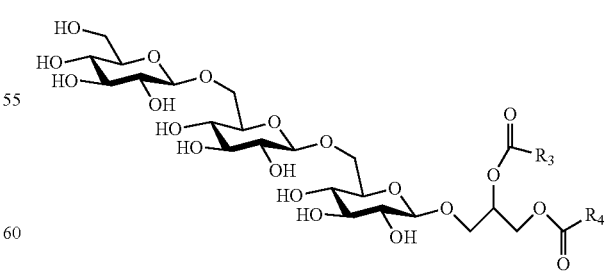

II wherein $R_3$ and $R_4$ are independently selected from a C14:0, C16:0, C16:1, C18:0, or C18:1 fatty acid, or any combination thereof and wherein one of $COR_3$ or $COR_4$ may be replaced by H.

23. The immunogenic composition of claim 15, wherein the LTA compound comprises the structure of Formula III

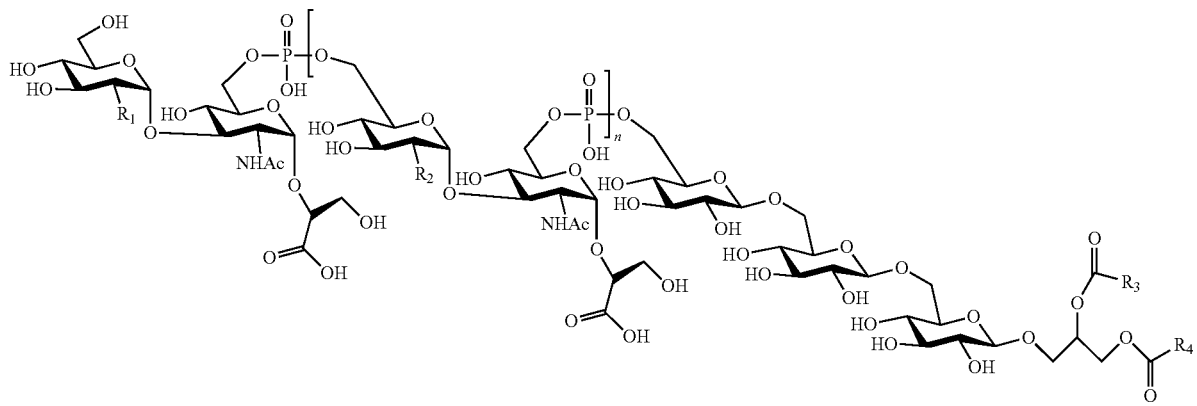

III wherein $R_1$ is selected from $NH_2$ and NHAc; each $R_2$ is independently selected from $NH_2$ and NHAc; n is an integer between about 1 and 20; $R_3$ and $R_4$ are independently selected from a C14:0, C16:0, C16:1, C18:0, or C18:1 fatty acid, or any combination thereof and wherein one of $COR_3$ or $COR_4$ may be replaced by H.

24. The immunogenic composition of claim 15, wherein the LTA compound comprises the structure of Formula IV:

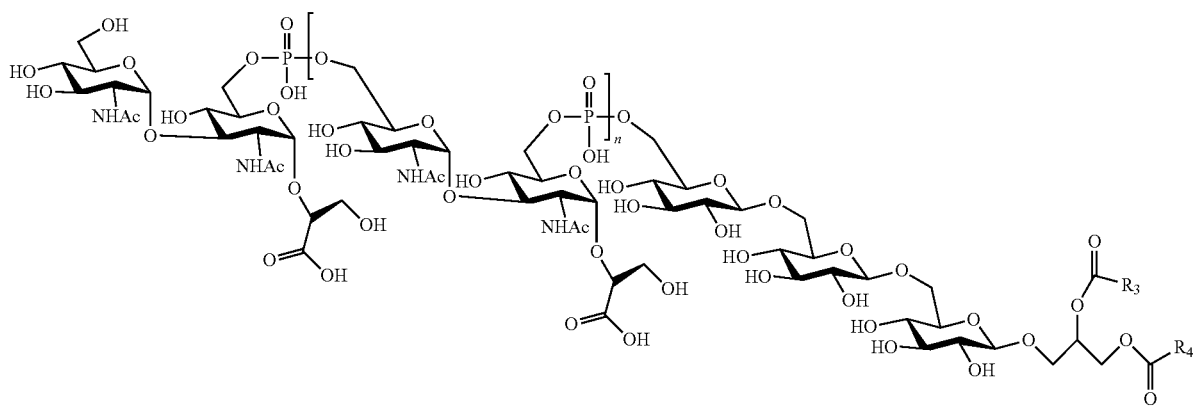

IV wherein n is an integer between 1 and 20, $R_3$ and $R_4$ are independently selected from a C14:0, C16:0, C16:1, C18:0, or C18:1 fatty acid or any combination thereof and wherein one of $COR_3$ or $COR_4$ may be replaced by H.

25. A method of inducing an immune response against *C. difficile* comprising administering an effective amount of the composition of claim 1 to a subject.

26. A method of inducing an immune response against *C. difficile* comprising administering an effective amount of the immunogenic composition of claim 11 to a subject.

27. A method of inducing an immune response against *C. difficile* comprising administering an effective amount the composition of claim 13 to a subject.

* * * * *